(12) United States Patent
Eggeling et al.

(10) Patent No.: US 7,732,176 B2
(45) Date of Patent: Jun. 8, 2010

(54) NUCLEOTIDE SEQUENCES THAT ENCODE DEREGULATED PHOSPHOGLYCERATE DEHYDROGENASES OF CORYNEFORM BACTERIA AND METHOD FOR PRODUCING L-SERINE

(75) Inventors: Lothar Eggeling, Julich (DE); Petra Peters-Wendisch, Jülich (DE); Roman Netzer, Jülich (DE); Hermann Sahm, Jülich (DE); Robert Faurie, Königslutter (DE); Birgit Klassen, Braunschweig (DE)

(73) Assignees: Forschungszentrum Julich GmbH, Julich (DE); Amino GmbH, Frellstedt (DE)

( * ) Notice: Subject to any disclaimer, the term of this patent is extended or adjusted under 35 U.S.C. 154(b) by 1168 days.

(21) Appl. No.: 10/520,999

(22) PCT Filed: Jul. 8, 2003

(86) PCT No.: PCT/DE03/02290

§ 371 (c)(1), (2), (4) Date: Jan. 6, 2006

(87) PCT Pub. No.: WO2004/007705

PCT Pub. Date: Jan. 22, 2004

(65) Prior Publication Data

US 2006/0106207 A1    May 18, 2006

(30) Foreign Application Priority Data

Jul. 10, 2002  (DE) .................... 102 31 297

(51) Int. Cl.
*C12N 9/00* (2006.01)
*C12N 9/04* (2006.01)
*C12N 9/12* (2006.01)
*C12P 13/06* (2006.01)

(52) U.S. Cl. ................ 435/183; 435/190; 435/194; 435/116

(58) Field of Classification Search ............... None
See application file for complete search history.

(56) References Cited

U.S. PATENT DOCUMENTS

| 5,624,828 | A  |   | 4/1997 | Katsumata et al. |
|-----------|-----|---|--------|------------------|
| 6,037,154 | A  | * | 3/2000 | Suga et al. ............. 435/116 |
| 6,180,373 | B1 |   | 1/2001 | Wich et al. |
| 6,258,573 | B1 | * | 7/2001 | Suga et al. ............. 435/116 |

FOREIGN PATENT DOCUMENTS

EP    0 943 687    9/1999

OTHER PUBLICATIONS

Bell et al. De-regulation of D-3-phosphoglycerate dehydrogenase by domain removal. Eur. J. Biochem. 269, 4176-4184 (2002).*
"3-Phosphoglycerate dehydrogenase . . . " by Peters-Wendisch et al. (Appl.Microbiol Biochtenol. (2002).
XP-001155222 ( C-terminal deletion . . . ) published by Elsevier Scioence Publishers 1991.
XP-002255655 published Oct. 2001.
XP-002255645 publiocation date Sep. 2002.

* cited by examiner

*Primary Examiner*—Andrew Wang
*Assistant Examiner*—Kagnew H Gebreyesus
(74) *Attorney, Agent, or Firm*—Andrew Wilford

(57) ABSTRACT

The invention relates to nucleotide sequences of coryneform bacteria that encode proteins that are involved in the biosynthesis of L-serine and to a method for producing L-serine. According to the invention, at least 79 amino acids at the C terminus of the wild-type serA sequence are deleted, thereby producing a 3-phosphoglycerate dehydrogenase having a reduced feedback inhibition by L-serine vis-à-vis the wild-type sequence.

28 Claims, 8 Drawing Sheets

*serA*

*serA*Δ79

*serA*Δ188

*serA*Δ197

*serA*Δ205

*serA*Δ211

Figure 1:
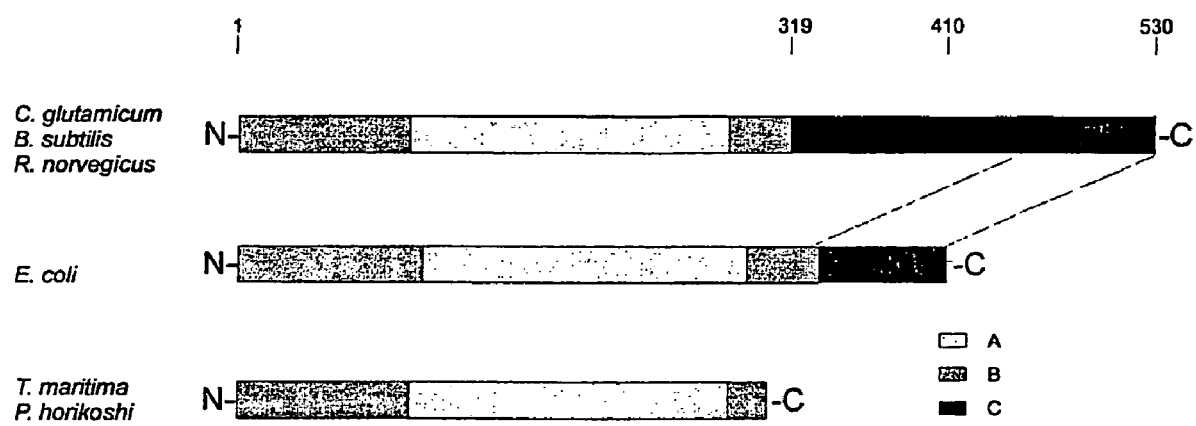

SEQUENCE LISTING

<160> NUMBER OF SEQ ID NOS: 19

<210> SEQ ID NO 1
<211> LENGTH: 1253
<212> TYPE: DNA
<213> ORGANISM: Corynebacterium glutamicum

<400> SEQUENCE: 1

| | |
|---|---|
| tctagagccg agacgtgaa taaaattcgc agctcattcc atcagcgtaa acgcagcttt | 60 |
| ttgcatggtg agacaccttt gggggtaaat ctcacagcat gaatctctgg gttagatgac | 120 |
| tttctgggtg ggggagggtt tagaatgttt ctagtcgcac gccaaaaccc ggcgtggaca | 180 |
| cgtctgcagc cgacgcggtc gtgcctgttg tagacggaca ttcctagttt ttccaggagt | 240 |
| aacttgtgag ccagaatggc cgtccggtag tcctcatcgc cgataagctt cgcagtcca | 300 |
| ctgttgacgc gcttggagat gcagtagaag tccgttgggt tgacggacct aaccgcccag | 360 |
| aactgcttga tgcagttaag gaagcggacg cactgctcgt gcgttctgct accactgtcg | 420 |
| atgctgaagt catcgccgct gcccctaact gaagatcgcg gtcgtgcc ggcgtgggct | 480 |
| tggacaacgt tgacatccct gctgccactg aagctggcgt catggttgct aacgcaccga | 540 |
| cctctaatat tcactccgct tgtgagcacg caatttcttt gctgctgtct actgctcgcc | 600 |
| agatccctgc tgctgatgcg acgctgcgtg agggcgagtg gaagcggtct tctttcaacg | 660 |
| gtgtggaaat tttcggaaaa actgtcggta tcgtcggttt tggccacatt ggtcagttgt | 720 |
| tgctcagcg tcttgctgcg tttgagacca ccattgttgc ttacgatcct tacgctaacc | 780 |
| ctgctcgtgc ggctcagctg aacgttgagt tggttgagtt ggatgagctg atgagccgtt | 840 |
| ctgactttgt caccattcac cttcctaaga ccaaggaaac tgctggcatg tttgatgcgc | 900 |
| agctccttgc taagtccaag aagggccaga tcatcatcaa cgctgctcgt ggtggccttg | 960 |
| ttgatgagca ggctttggct gatgcgattg agtccggtca cattcgtggc gctggtttcg | 1020 |
| atgtgtactc caccgagcct tgcactgatt ctcctttgtt caagttgcct caggttgttg | 1080 |
| tgactcctca cttgggtgct tctactgaag aggctcagga tcgtgcgggt actgacgttg | 1140 |
| ctgattctgt gctcaaggcg ctggctggcg agttcgtggc ggatgctgtg aacgtttccg | 1200 |
| gtggtcgcgt gggcgaagag gttgctgtgt ggatggatct ggcttaagga tcc | 1253 |

<210> SEQ ID NO 2
<211> LENGTH: 1607
<212> TYPE: DNA
<213> ORGANISM: Corynebacterium glutamicum

<400> SEQUENCE: 2

| | |
|---|---|
| tctagagccg agacgtgaa taaaattcgc agctcattcc atcagcgtaa acgcagcttt | 60 |
| ttgcatggtg agacaccttt gggggtaaat ctcacagcat gaatctctgg gttagatgac | 120 |
| tttctgggtg ggggagggtt tagaatgttt ctagtcgcac gccaaaaccc ggcgtggaca | 180 |
| cgtctgcagc cgacgcggtc gtgcctgttg tagacggaca ttcctagttt ttccaggagt | 240 |
| aacttgtgag ccagaatggc cgtccggtag tcctcatcgc cgataagctt cgcagtcca | 300 |
| ctgttgacgc gcttggagat gcagtagaag tccgttgggt tgacggacct aaccgcccag | 360 |
| aactgcttga tgcagttaag gaagcggacg cactgctcgt gcgttctgct accactgtcg | 420 |
| atgctgaagt catcgccgct gcccctaact gaagatcgcg gtcgtgcc ggcgtgggct | 480 |
| tggacaacgt tgacatccct gctgccactg aagctggcgt catggttgct aacgcaccga | 540 |

```
cctctaatat tcactccgct tgtgagcacg caatttcttt gctgctgtct actgctcgcc      600
agatccctgc tgctgatgcg acgctgcgtg agggcgagtg aagcggtct tctttcaacg       660 gtgtggaaat tttcggaaaa actgtcggta tcgtcggttt tggccacatt ggtcagttgt     720
ttgctcagcg tcttgctgcg tttgagacca ccattgttgc ttacgatcct tacgctaacc     780
ctgctcgtgc ggctcagctg aacgttgagt tggttgagtt ggatgagctg atgagccgtt    840
ctgactttgt caccattcac cttcctaaga ccaaggaaac tgctggcatg tttgatgcgc    900
agctccttgc taagtccaag aagggccaga tcatcatcaa cgctgctcgt ggtggccttg    960
ttgatgagca ggctttggct gatgcgattg agtccggtca cattcgtggc gctggtttcg   1020
atgtgtactc caccgagcct tgcactgatt ctcctttgtt caagttgcct caggttgttg   1080
tgactcctca cttgggtgct tctactgaag aggctcagga tcgtgcgggt actgacgttg   1140
ctgattctgt gctcaaggcg ctggctggcg agttcgtggc ggatgctgtg aacgtttccg   1200
gtggtcgcgt gggcgaagag gttgctgtgt ggatggatct ggctcgcaag cttggtcttc   1260
ttgctggcaa gcttgtcgac gccgccccag tctccattga ggttgaggct cgaggcgagc   1320
tttcttccga gcaggtcgat gcacttggtt tgtccgctgt tcgtggtttg ttctccggaa   1380
ttatcgaaga gtccgttact ttcgtcaacg ctcctcgcat tgctgaagag cgtggcctgg   1440
acatctccgt gaagaccaac tctgagtctg ttactcaccg ttccgtcctg caggtcaagg   1500
tcattactgg cagcggcgcg agcgcaactg ttgttggtgc cctgactggt cttgagcgcg   1560
ttgagaagat cacccgcatc aatggccgtg gcctggatta aggatcc              1607

<210> SEQ ID NO 3
<211> LENGTH: 1280
<212> TYPE: DNA
<213> ORGANISM: Corynebacterium glutamicum

<400> SEQUENCE: 3
tctagagccg gagacgtgaa taaaattcgc agctcattcc atcagcgtaa acgcagcttt      60
ttgcatggtg agacaccttt gggggtaaat ctcacagcat gaatctctgg gttagatgac    120
tttctgggtg ggggagggtt tagaatgttt ctagtcgcac gccaaaaccc ggcgtggaca    180
cgtctgcagc cgacgcggtc gtgcctgttg tagacggaca ttcctagttt ttccaggagt    240
aacttgtgag ccagaatggc cgtccggtag tcctcatcgc cgataagctt gcgcagtcca    300
ctgttgacgc gcttggagat gcagtagaag tccgttgggt tgacggacct aaccgcccag    360
aactgcttga tgcagttaag gaagcggacg cactgctcgt gcgttctgct accactgtcg    420
atgctgaagt catcgccgct gcccctaact tgaagatcgt cggtcgtgcc ggcgtgggct    480
tggacaacgt tgacatccct gctgccactg aagctggcgt catggttgct aacgcaccga    540
cctctaatat tcactccgct tgtgagcacg caatttcttt gctgctgtct actgctcgcc    600
agatccctgc tgctgatgcg acgctgcgtg agggcgagtg aagcggtct tctttcaacg     660 gtgtggaaat tttcggaaaa actgtcggta tcgtcggttt tggccacatt ggtcagttgt    720
ttgctcagcg tcttgctgcg tttgagacca ccattgttgc ttacgatcct tacgctaacc    780
ctgctcgtgc ggctcagctg aacgttgagt tggttgagtt ggatgagctg atgagccgtt    840
ctgactttgt caccattcac cttcctaaga ccaaggaaac tgctggcatg tttgatgcgc    900
agctccttgc taagtccaag aagggccaga tcatcatcaa cgctgctcgt ggtggccttg    960
ttgatgagca ggctttggct gatgcgattg agtccggtca cattcgtggc gctggtttcg   1020
atgtgtactc caccgagcct tgcactgatt ctcctttgtt caagttgcct caggttgttg   1080
```

-continued

| | |
|---|---|
| tgactcctca cttgggtgct tctactgaag aggctcagga tcgtgcgggt actgacgttg | 1140 |
| ctgattctgt gctcaaggcg ctggctggcg agttcgtggc ggatgctgtg aacgtttccg | 1200 |
| gtggtcgcgt gggcgaagag gttgctgtgt ggatggatct ggctcgcaag cttggtcttc | 1260 |
| ttgctggcaa gtaaggatcc | 1280 |

<210> SEQ ID NO 4
<211> LENGTH: 1229
<212> TYPE: DNA
<213> ORGANISM: Corynebacterium glutamicum

<400> SEQUENCE: 4

| | |
|---|---|
| tctagagccg agacgtgaa taaaattcgc agctcattcc atcagcgtaa acgcagcttt | 60 |
| ttgcatggtg agacaccttt ggggtaaat ctcacagcat gaatctctgg gttagatgac | 120 |
| tttctgggtg ggggagggtt tagaatgttt ctagtcgcac gccaaaaccc ggcgtggaca | 180 |
| cgtctgcagc cgacgcggtc gtgcctgttg tagacgggaca ttcctagttt ttccaggagt | 240 |
| aacttgtgag ccagaatggc cgtccggtag tcctcatcgc cgataagctt gcgcagtcca | 300 |
| ctgttgacgc gcttggagat gcagtagaag tccgttgggt tgacggacct aaccgcccag | 360 |
| aactgcttga tgcagttaag gaagcggacg cactgctcgt gcgttctgct accactgtcg | 420 |
| atgctgaagt catcgccgct gcccctaact gaagatcgct cggtcgtgcc ggcgtgggct | 480 |
| tggacaacgt tgacatccct gctgccactg aagctggcgt catggttgct aacgcaccga | 540 |
| cctctaatat tcactccgct tgtgagcacg caatttcttt gctgctgtct actgctcgcc | 600 |
| agatccctgc tgctgatgcg acgctgcgtg agggcgagtg gaagcggtct tcttttcaacg | 660 |
| gtgtggaaat tttcggaaaaa actgtcggta tcgtcggttt tggccacatt ggtcagttgt | 720 |
| ttgctcagcg tcttgctgcg tttgagacca ccattgttgc ttacgatcct tacgctaacc | 780 |
| ctgctcgtgc ggctcagctg aacgttgagt tggttgagtt ggatgagctg atgagccgtt | 840 |
| ctgactttgt caccattcac cttcctaaga ccaaggaaac tgctggcatg tttgatgcgc | 900 |
| agctccttgc taagtccaag aagggccaga tcatcatcaa cgctgctcgt ggtggccttg | 960 |
| ttgatgagca ggctttggct gatgcgattg agtccggtca cattcgtggc gctggtttcg | 1020 |
| atgtgtactc caccgagcct tgcactgatt ctcctttgtt caagttgcct caggttgttg | 1080 |
| tgactcctca cttgggtgct tctactgaag aggctcagga tcgtgcgggt actgacgttg | 1140 |
| ctgattctgt gctcaaggcg ctggctggcg agttcgtggc ggatgctgtg aacgtttccg | 1200 |
| gtggtcgcgt gggcgaagag taaggatcc | 1229 |

<210> SEQ ID NO 5
<211> LENGTH: 1211
<212> TYPE: DNA
<213> ORGANISM: Corynebacterium glutamicum

<400> SEQUENCE: 5

| | |
|---|---|
| tctagagccg agacgtgaa taaaattcgc agctcattcc atcagcgtaa acgcagcttt | 60 |
| ttgcatggtg agacaccttt ggggtaaat ctcacagcat gaatctctgg gttagatgac | 120 |
| tttctgggtg ggggagggtt tagaatgttt ctagtcgcac gccaaaaccc ggcgtggaca | 180 |
| cgtctgcagc cgacgcggtc gtgcctgttg tagacgggaca ttcctagttt ttccaggagt | 240 |
| aacttgtgag ccagaatggc cgtccggtag tcctcatcgc cgataagctt gcgcagtcca | 300 |
| ctgttgacgc gcttggagat gcagtagaag tccgttgggt tgacggacct aaccgcccag | 360 |
| aactgcttga tgcagttaag gaagcggacg cactgctcgt gcgttctgct accactgtcg | 420 |

```
atgctgaagt catcgccgct gccccctaact tgaagatcgt cggtcgtgcc ggcgtgggct    480
tggacaacgt tgacatccct gctgccactg aagctggcgt catggttgct aacgcaccga    540
cctctaatat tcactccgct tgtgagcacg caatttcttt gctgctgtct actgctcgcc    600
agatccctgc tgctgatgcg acgctgcgtg agggcgagtg aagcggtct tctttcaacg    660 gtgtggaaat tttcggaaaa actgtcggta tcgtcggttt tggccacatt ggtcagttgt    720
ttgctcagcg tcttgctgcg tttgagacca ccattgttgc ttacgatcct tacgctaacc    780
ctgctcgtgc ggctcagctg aacgttgagt tggttgagtt ggatgagctg atgagccgtt    840
ctgactttgt caccattcac cttcctaaga ccaaggaaac tgctggcatg tttgatgcgc    900
agctccttgc taagtccaag aagggccaga tcatcatcaa cgctgctcgt ggtggccttg    960
ttgatgagca ggctttggct gatgcgattg agtccggtca cattcgtggc gctggtttcg   1020
atgtgtactc caccgagcct tgcactgatt ctccttttgtt caagttgcct caggttgttg   1080
tgactcctca cttgggtgct tctactgaag aggctcagga tcgtgcgggt actgacgttg   1140
ctgattctgt gctcaaggcg ctggctggcg agttcgtggc ggatgctgtg aacgtttccg   1200
gttaaggatc c                                                        1211

<210> SEQ ID NO 6
<211> LENGTH: 2043
<212> TYPE: DNA
<213> ORGANISM: Corynebacterium glutamicum

<400> SEQUENCE: 6
tctagagccg gagacgtgaa taaaattcgc agctcattcc atcagcgtaa acgcagcttt     60
ttgcatggtg agacaccttt gggggtaaat ctcacagcat gaatctctgg gttagatgac    120
tttctgggtg ggggagggtt tagaatgttt ctagtcgcac gccaaaaccc ggcgtggaca    180
cgtctgcagc cgacgcggtc gtgcctgttg tagacggaca ttcctagttt ttccaggagt    240
aacttgtgag ccagaatggc cgtccggtag tcctcatcgc cgataagctt gcgcagtcca    300
ctgttgacgc gcttggagat gcagtagaag tccgttgggt tgacggacct aaccgcccag    360
aactgcttga tgcagttaag gaagcggacg cactgctcgt gcgttctgct accactgtcg    420
atgctgaagt catcgccgct gccccctaact tgaagatcgt cggtcgtgcc ggcgtgggct    480
tggacaacgt tgacatccct gctgccactg aagctggcgt catggttgct aacgcaccga    540
cctctaatat tcactccgct tgtgagcacg caatttcttt gctgctgtct actgctcgcc    600
agatccctgc tgctgatgcg acgctgcgtg agggcgagtg aagcggtct tctttcaacg    660 gtgtggaaat tttcggaaaa actgtcggta tcgtcggttt tggccacatt ggtcagttgt    720
ttgctcagcg tcttgctgcg tttgagacca ccattgttgc ttacgatcct tacgctaacc    780
ctgctcgtgc ggctcagctg aacgttgagt tggttgagtt ggatgagctg atgagccgtt    840
ctgactttgt caccattcac cttcctaaga ccaaggaaac tgctggcatg tttgatgcgc    900
agctccttgc taagtccaag aagggccaga tcatcatcaa cgctgctcgt ggtggccttg    960
ttgatgagca ggctttggct gatgcgattg agtccggtca cattcgtggc gctggtttcg   1020
atgtgtactc caccgagcct tgcactgatt ctccttttgtt caagttgcct caggttgttg   1080
tgactcctca cttgggtgct tctactgaag aggctcagga tcgtgcgggt actgacgttg   1140
ctgattctgt gctcaaggcg ctggctggcg agttcgtggc ggatgctgtg aacgtttccg   1200
gtggtcgcgt gggcgaagag gttgctgtgt ggatggatct ggctcgcaag cttggtcttc   1260
ttgctggcaa gcttgtcgac gccgccccag tctccattga ggttgaggct cgaggcgagc   1320
```

```
tttcttccga gcaggtcgat gcacttggtt tgtccgctgt tcgtggtttg ttctccggaa   1380
ttatcgaaga gtccgttact ttcgtcaacg ctcctcgcat tgctgaagag cgtggcctgg   1440
acatctccgt gaagaccaac tctgagtctg ttactcaccg ttccgtcctg caggtcaagg   1500
tcattactgg cagcggcgcg agcgcaactg ttgttggtgc cctgactggt cttgagcgcg   1560
ttgagaagat cacccgcatc aatggccgtg gcctggatct gcgcgcagag ggtctgaacc   1620
tcttcctgca gtacactgac gctcctggtg cactgggtac cgttggtacc aagctgggtg   1680
ctgctggcat caacatcgag gctgctgcgt tgactcaggc tgagaagggt gacggcgctg   1740
tcctgatcct gcgtgttgag tccgctgtct ctgaagagct ggaagctgaa atcaacgctg   1800
agttgggtgc tacttccttc caggttgatc ttgactaatt agagatccat ttgcttgaac   1860
cgccttccca tctttgaatt cattcaaggt ggtaaggcgg ttttcgctct tttaatacag   1920
ttttaaaggt agatttggga gagaagattt cccttaagaa aggttcttaa caaccatgcc   1980
gcctgcgacg ctgttcaatg ttttgacttc agctggactt gaccctcacc agtctaagga   2040
tcc                                                                2043
```

<210> SEQ ID NO 7
<211> LENGTH: 333
<212> TYPE: PRT
<213> ORGANISM: Corynebacterium glutamicum

<400> SEQUENCE: 7

```
Met Ser Gln Asn Gly Arg Pro Val Val Leu Ile Ala Asp Lys Leu Ala
  1               5                  10                  15

Gln Ser Thr Val Asp Ala Leu Gly Asp Ala Val Glu Val Arg Trp Val
             20                  25                  30

Asp Gly Pro Asn Arg Pro Glu Leu Leu Asp Ala Val Lys Glu Ala Asp
         35                  40                  45

Ala Leu Leu Val Arg Ser Ala Thr Thr Val Asp Ala Glu Val Ile Ala
     50                  55                  60

Ala Ala Pro Asn Leu Lys Ile Val Gly Arg Ala Gly Val Gly Leu Asp
 65                  70                  75                  80

Asn Val Asp Ile Pro Ala Ala Thr Glu Ala Gly Val Met Val Ala Asn
                 85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205

Thr Lys Glu Thr Ala Gly Met Phe Asp Ala Gln Leu Leu Ala Lys Ser
    210                 215                 220

Lys Lys Gly Gln Ile Ile Ile Asn Ala Ala Arg Gly Gly Leu Val Asp
225                 230                 235                 240
```

```
Glu Gln Ala Leu Ala Asp Ala Ile Glu Ser Gly His Ile Arg Gly Ala
            245                 250                 255

Gly Phe Asp Val Tyr Ser Thr Glu Pro Cys Thr Asp Ser Pro Leu Phe
            260                 265                 270

Lys Leu Pro Gln Val Val Val Thr Pro His Leu Gly Ala Ser Thr Glu
            275                 280                 285

Glu Ala Gln Asp Arg Ala Gly Thr Asp Val Ala Asp Ser Val Leu Lys
            290                 295                 300

Ala Leu Ala Gly Glu Phe Val Ala Asp Ala Val Asn Val Ser Gly Gly
305                 310                 315                 320

Arg Val Gly Glu Glu Val Ala Val Trp Met Asp Leu Ala
            325                 330

<210> SEQ ID NO 8
<211> LENGTH: 451
<212> TYPE: PRT
<213> ORGANISM: Corynebacterium glutamicum

<400> SEQUENCE: 8

Met Ser Gln Asn Gly Arg Pro Val Val Leu Ile Ala Asp Lys Leu Ala
1               5                   10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Ala Val Lys Glu Ala Asp
            35                  40                  45

Ala Leu Leu Val Arg Ser Ala Thr Thr Val Asp Ala Glu Val Ile Ala
        50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
            115                 120                 125

Glu Gly Glu Trp Lys Arg Ser Ser Phe Asn Gly Val Glu Ile Phe Gly
        130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
            195                 200                 205

Thr Lys Glu Thr Ala Gly Met Phe Asp Ala Gln Leu Leu Ala Lys Ser
        210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
            245                 250                 255

Gly Phe Asp Val Tyr Ser Thr Glu Pro Cys Thr Asp Ser Pro Leu Phe
            260                 265                 270

Lys Leu Pro Gln Val Val Val Thr Pro His Leu Gly Ala Ser Thr Glu
            275                 280                 285
```

```
Glu Ala Gln Asp Arg Ala Gly Thr Asp Val Ala Asp Ser Val Leu Lys
    290                 295                 300

Ala Leu Ala Gly Glu Phe Val Ala Asp Ala Val Asn Val Ser Gly Gly
305                 310                 315                 320

Arg Val Gly Glu Val Ala Val Trp Met Asp Leu Ala Arg Lys Leu
                325                 330                 335

Gly Leu Leu Ala Gly Lys Leu Val Asp Ala Pro Val Ser Ile Glu
            340                 345                 350

Val Glu Ala Arg Gly Glu Leu Ser Ser Glu Gln Val Asp Ala Leu Gly
        355                 360                 365

Leu Ser Ala Val Arg Gly Leu Phe Ser Gly Ile Ile Glu Glu Ser Val
    370                 375                 380

Thr Phe Val Asn Ala Pro Arg Ile Ala Glu Glu Arg Gly Leu Asp Ile
385                 390                 395                 400

Ser Val Lys Thr Asn Ser Glu Ser Val Thr His Arg Ser Val Leu Gln
                405                 410                 415

Val Lys Val Ile Thr Gly Ser Gly Ala Ser Ala Thr Val Val Gly Ala
            420                 425                 430

Leu Thr Gly Leu Glu Arg Val Glu Lys Ile Thr Arg Ile Asn Gly Arg
        435                 440                 445

Gly Leu Asp
    450

<210> SEQ ID NO 9
<211> LENGTH: 342
<212> TYPE: PRT
<213> ORGANISM: Corynebacterium glutamicum

<400> SEQUENCE: 9

Met Ser Gln Asn Gly Arg Pro Val Val Leu Ile Ala Asp Lys Leu Ala
1               5                   10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Ala Val Lys Glu Ala Asp
        35                  40                  45

Ala Leu Leu Val Arg Ser Ala Thr Thr Val Asp Ala Glu Val Ile Ala
    50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205
```

```
Thr Lys Glu Thr Ala Gly Met Phe Asp Ala Gln Leu Leu Ala Lys Ser
    210                 215                 220
Lys Lys Gly Gln Ile Ile Ile Asn Ala Ala Arg Gly Gly Leu Val Asp
225                 230                 235                 240
Glu Gln Ala Leu Ala Asp Ala Ile Glu Ser Gly His Ile Arg Gly Ala
                245                 250                 255
Gly Phe Asp Val Tyr Ser Thr Glu Pro Cys Thr Asp Ser Pro Leu Phe
            260                 265                 270
Lys Leu Pro Gln Val Val Thr Pro His Leu Gly Ala Ser Thr Glu
        275                 280                 285
Glu Ala Gln Asp Arg Ala Gly Thr Asp Val Ala Asp Ser Val Leu Lys
        290                 295                 300
Ala Leu Ala Gly Glu Phe Val Asp Ala Val Asn Val Ser Gly Gly
305                 310                 315                 320
Arg Val Gly Glu Glu Val Ala Val Trp Met Asp Leu Ala Arg Lys Leu
                325                 330                 335
Gly Leu Leu Ala Gly Lys
            340

<210> SEQ ID NO 10
<211> LENGTH: 325
<212> TYPE: PRT
<213> ORGANISM: Corynebacterium glutamicum

<400> SEQUENCE: 10

Met Ser Gln Asn Gly Arg Pro Val Val Leu Ile Ala Asp Lys Leu Ala
1               5                   10                  15
Gln Ser Thr Val Asp Ala Leu Gly Asp Ala Val Glu Val Arg Trp Val
            20                  25                  30
Asp Gly Pro Asn Arg Pro Glu Leu Leu Asp Ala Val Lys Glu Ala Asp
        35                  40                  45
Ala Leu Leu Val Arg Ser Ala Thr Thr Val Asp Ala Glu Val Ile Ala
    50                  55                  60
Ala Ala Pro Asn Leu Lys Ile Val Gly Arg Ala Gly Val Gly Leu Asp
65                  70                  75                  80
Asn Val Asp Ile Pro Ala Ala Thr Glu Ala Gly Val Met Val Ala Asn
                85                  90                  95
Ala Pro Thr Ser Asn Ile His Ser Ala Cys Glu His Ala Ile Ser Leu
            100                 105                 110
Leu Leu Ser Thr Ala Arg Gln Ile Pro Ala Ala Asp Ala Thr Leu Arg
        115                 120                 125
Glu Gly Glu Trp Lys Arg Ser Ser Phe Asn Gly Val Glu Ile Phe Gly
    130                 135                 140
Lys Thr Val Gly Ile Val Gly Phe Gly His Ile Gly Gln Leu Phe Ala
145                 150                 155                 160
Gln Arg Leu Ala Ala Phe Glu Thr Thr Ile Val Ala Tyr Asp Pro Tyr
                165                 170                 175
Ala Asn Pro Ala Arg Ala Ala Gln Leu Asn Val Glu Leu Val Glu Leu
            180                 185                 190
Asp Glu Leu Met Ser Arg Ser Asp Phe Val Thr Ile His Leu Pro Lys
        195                 200                 205
Thr Lys Glu Thr Ala Gly Met Phe Asp Ala Gln Leu Leu Ala Lys Ser
    210                 215                 220
Lys Lys Gly Gln Ile Ile Ile Asn Ala Ala Arg Gly Gly Leu Val Asp
225                 230                 235                 240
```

```
Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
                260                 265                 270

Lys Leu Pro Gln Val Val Thr Pro His Leu Gly Ala Ser Thr Glu
            275                 280                 285

Glu Ala Gln Asp Arg Ala Gly Thr Asp Val Ala Asp Ser Val Leu Lys
            290                 295                 300

Ala Leu Ala Gly Glu Phe Val Ala Asp Ala Val Asn Val Ser Gly Gly
305                 310                 315                 320

Arg Val Gly Glu Glu
                325

<210> SEQ ID NO 11
<211> LENGTH: 319
<212> TYPE: PRT
<213> ORGANISM: Corynebacterium glutamicum

<400> SEQUENCE: 11

Met Ser Gln Asn Gly Arg Pro Val Val Leu Ile Ala Asp Lys Leu Ala
  1               5                  10                  15

Gln Ser Thr Val Asp Ala Leu Gly Asp Ala Val Glu Val Arg Trp Val
                 20                  25                  30

Asp Gly Pro Asn Arg Pro Glu Leu Leu Asp Ala Val Lys Glu Ala Asp
             35                  40                  45

Ala Leu Leu Val Arg Ser Ala Thr Thr Val Asp Ala Glu Val Ile Ala
         50                  55                  60

Ala Ala Pro Asn Leu Lys Ile Val Gly Arg Ala Gly Val Gly Leu Asp
 65                  70                  75                  80

Asn Val Asp Ile Pro Ala Ala Thr Glu Ala Gly Val Met Val Ala Asn
                 85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205

Thr Lys Glu Thr Ala Gly Met Phe Asp Ala Gln Leu Leu Ala Lys Ser
    210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
                260                 265                 270

Lys Leu Pro Gln Val Val Thr Pro His Leu Gly Ala Ser Thr Glu
            275                 280                 285
```

```
Glu Ala Gln Asp Arg Ala Gly Thr Asp Val Ala Asp Ser Val Leu Lys
        290                 295                 300

Ala Leu Ala Gly Glu Phe Val Ala Asp Ala Val Asn Val Ser Gly
305                 310                 315
```

<210> SEQ ID NO 12
<211> LENGTH: 530
<212> TYPE: PRT
<213> ORGANISM: Corynebacterium glutamicum

<400> SEQUENCE: 12

```
Met Ser Gln Asn Gly Arg Pro Val Val Leu Ile Ala Asp Lys Leu Ala
 1               5                  10                  15

Gln Ser Thr Val Asp Ala Leu Gly Asp Ala Val Glu Val Arg Trp Val
                20                  25                  30

Asp Gly Pro Asn Arg Pro Glu Leu Leu Asp Ala Val Lys Glu Ala Asp
            35                  40                  45

Ala Leu Leu Val Arg Ser Ala Thr Thr Val Asp Ala Glu Val Ile Ala
        50                  55                  60

Ala Ala Pro Asn Leu Lys Ile Val Gly Arg Ala Gly Val Gly Leu Asp
 65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205

Thr Lys Glu Thr Ala Gly Met Phe Asp Ala Gln Leu Leu Ala Lys Ser
    210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
            260                 265                 270

Lys Leu Pro Gln Val Val Val Thr Pro His Leu Gly Ala Ser Thr Glu
        275                 280                 285

Glu Ala Gln Asp Arg Ala Gly Thr Asp Val Ala Asp Ser Val Leu Lys
    290                 295                 300

Ala Leu Ala Gly Glu Phe Val Ala Asp Ala Val Asn Val Ser Gly Gly
305                 310                 315                 320

Arg Val Gly Glu Glu Val Ala Val Trp Met Asp Leu Ala Arg Lys Leu
                325                 330                 335

Gly Leu Leu Ala Gly Lys Leu Val Asp Ala Ala Pro Val Ser Ile Glu
            340                 345                 350
```

```
Val Glu Ala Arg Gly Glu Leu Ser Ser Glu Gln Val Asp Ala Leu Gly
        355                 360                 365

Leu Ser Ala Val Arg Gly Leu Phe Ser Gly Ile Ile Glu Glu Ser Val
    370                 375                 380

Thr Phe Val Asn Ala Pro Arg Ile Ala Glu Glu Arg Gly Leu Asp Ile
385                 390                 395                 400

Ser Val Lys Thr Asn Ser Glu Ser Val Thr His Arg Ser Val Leu Gln
                405                 410                 415

Val Lys Val Ile Thr Gly Ser Gly Ala Ser Ala Thr Val Val Gly Ala
            420                 425                 430

Leu Thr Gly Leu Glu Arg Val Glu Lys Ile Thr Arg Ile Asn Gly Arg
        435                 440                 445

Gly Leu Asp Leu Arg Ala Glu Gly Leu Asn Leu Phe Leu Gln Tyr Thr
    450                 455                 460

Asp Ala Pro Gly Ala Leu Gly Thr Val Gly Thr Lys Leu Gly Ala Ala
465                 470                 475                 480

Gly Ile Asn Ile Glu Ala Ala Leu Thr Gln Ala Glu Lys Gly Asp
                485                 490                 495

Gly Ala Val Leu Ile Leu Arg Val Glu Ser Ala Val Ser Glu Glu Leu
            500                 505                 510

Glu Ala Glu Ile Asn Ala Glu Leu Gly Ala Thr Ser Phe Gln Val Asp
        515                 520                 525

Leu Asp
    530

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 13
tctagagccg gagacgtgaa taaaat                                          26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 14
ggatccgact ggtgagggtc aagtcc                                          26

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 15
ggatccttaa ccggaaacgt tcacagc                                         27
```

-continued

```
<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 16
ggatccttac tcttcgccca cgcgacc                                            27

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 17 ggataccttaa agccagaatc catccacaca g                                      31

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 18
ggatccttac ttgccagcaa gaaaagacc                                          29

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 19
ggatccttaa tccaggccac ggccatt                                            27
```

NUCLEOTIDE SEQUENCES THAT ENCODE DEREGULATED PHOSPHOGLYCERATE DEHYDROGENASES OF CORYNEFORM BACTERIA AND METHOD FOR PRODUCING L-SERINE

CROSS REFERENCE TO RELATED APPLICATIONS

This application is the US national phase of PCT application PCT/DE2003/002290 filed 8 Jul. 2003 with a claim to the priority of German patent application 10231297.4 itself filed 10 Jul. 2002.

The invention relates to the nucleotide sequences of coryneform bacteria coding for proteins participating in the biosynthesis of L-serine and a method of producing L-serine.

The amino acid L-serine finds use in the food industry, the animal feed industry and the pharmaceutical industry as well as in human medicine. In addition it functions as a building block for the synthesis of other industrially valuable products like for example L-tryptophane from indole and L-serine.

It is known that L-serine can be produced by the fermentation of a coryneform bacteria strain. So for example a strain of *Corynebacterium glycinophilum* can form L-serine from glycine and carbohydrates (Kubota K, Kageyama K, Shiro T and Okumura S (1971) Journal of General Applications in Microbiology, 17: 167-168; Kubota K, Kageyama K, Maeyashiki I, Yamada K and Okumura S (1972) Journal of General Applications in Microbiology 18:365).

In the conversion of glycine to L-serine, there is here a participation of the enzyme L-serine-hydroxymethyl-transferase (Kubota K and Yokozeki K (1989) Journal of Fermentation and Bioengineering, 67(6): 387-390). The strain which is used however is associated with a reduced L-serine proteolysis which can lead to a reduction in the activity of the enzyme L-serine-dehydratase (Kubota K, Kageyama K, Shiro T and Okumura S (1971) Journal of General Applications in Microbiology, 17: 167-168; Kubota K, (1985) Agricultural Biological Chemistry 49:7-12).

Furthermore, L-serine is produced fermentatively from methanol and glycine with the assistance of methylotrophic bacteria like for example *Hyphomicrobium* lines (Izumi Y, Yoshida Tm Nutazaju Ssm Nutsybaga T, Igsguri T, Shiamo M, Miyata A and Tanabe T (1993) Applied Microbiology and Biotechnology, 39: 427-432). In both cases the amino acid glycine must be introduced as a precursor for the formation of the amino acid L-serine.

Furthermore, *Coryneform* bacteria are known which can produce the L-serine directly from carbohydrates without adding precursors. These lines belong to the *Corynebacterium glutamicum* species which are characterized by the fact that they are for example resistant with respect to the L-serine analog serine-hydroxamate and β-chloroalanine and are subject to undirected mutagenesis (Yoshida H and Nakayama K (1974) Nihon-Nogei-Kagakukaishi 48: 201-208).

In addition, *Brevibacterium flavum* strains are known which by undirected mutagenesis show defects in the L-serine proteolysis, an increased activity of the serA-coded 3-phosphoglycerate-dehydrogenase and which overexpress the genes serB and serC which derive from *Escherichia coli* (EP 0 931833A2). The deregulated serA gene which is thus used is recovered from indirect mutagenesis and differs from the wild type gene only by a single replacement. The expression of this gene has the disadvantage that it easily reverts and thus can pass back into the regulated state.

A drawback of earlier known 3-phosphoglycerate dehydrogenases lies in its feed-back inhibition by L-serine, which, for example, reduces the productivity of the microbial production of L-serine. The region which answers for this regulation by L-serine is the C-terminus of the protein. From WO 93/12235, a DNA is known which codes for a 3-phosphoglycerate-dehydrogenase from *E. coli* whose C-terminus is modified by up to 25%, is completely deleted or is subject to an insertion in a specific region so that the L-serine induced inhibition is reduced. This 3-phosphoglycerate dehydrogenase has however only a small activity. An improved L-serine production cannot be obtained with the deregulated 3-phosphoglycerate-dehydrogenase.

The wild type SerA sequence is generally known and can be obtained from data bases known in the art to the artisan or seen in the accompanying sequence protocol in SEQ ID No. 6 of the accompanying sequence protocol.

It is thus an object of the invention to provide features which enable the aforementioned drawbacks to be obviated and which will give rise to an improved production of L-serine or metabolic products derived therefrom, like for example tryptophane. It is thus also an object of the invention to provide nucleic acids coding for a 3-phosphoglycerate-dehydrogenase which, by comparison to naturally available 3-phosphoglycerate-dehydrogenase has a reduced feedback inhibition through L-serine while maintaining the activity. In this connection it is a further object of the invention to provide a 3-phosphoglycerate-dehydrogenase and microorganisms which by comparison with naturally available 3-phosphoglycerate-dehydrogenase or microorganisms with a 3-phosphoglycerate-dehydrogenase, which will have reduced feedback inhibition by L-serine while maintaining the activity. Furthermore, it is an object of the invention to provide an improved method for the production of L-serine.

The objects are attained according to the invention with the modified polynucleotides having SEQ ID NO:1, SEQ ID NO:2, SEQ ID NO:3, SEQ ID NO:4, and SEQ ID NO:5, each expressing a modified 3-phosphoglycerate-dehydrogenase (PGD). Furthermore, the objects are attained in accordance with the invention as described above along with regulating sequences, operatively linked to said polynucleotides.

With the nucleic acids according to the invention and the polypeptides it is possible directly to obtain a 3-phosphoglycerate dehydrogenase which, by contrast with naturally available nucleic acids or enzymes or nucleic acids or enzymes which are not modified by gene technology, which have no feedback inhibition, while maintaining the 3-phosphoglycerate-dehydrogenase activity. These characteristics are referred to below as "deregulated" collectively. Furthermore, it is possible to prepare microorganisms and provide a process whereby L-serine production has higher yields by comparison to previously known microbial processes.

Further features are given in the dependent claims.

The subject matter of the invention is the preparation of nucleic acids coding for a deregulated 3-phosphoglycerate-dehydrogenase indicated below by PGD and containing a gene sequence serA according to SEQ ID No 1, 2, 3, 4 or 5 or an allele, homologue or derivative of these nucleotide sequences which hybridizes therewith. The nucleic acid according to SEQ ID No. 1 which codes for a PGD with a deletion of 197 amino acids at the C-terminus has been found to be particularly advantageous.

The nucleic acids according to the invention are characterized in that they can be isolated from coryneform bacteria, especially of the geneva *Corynebacterium* or *Brevibacterium* and especially preferably from *Corynebacterium glutamicum*. As examples of the culture lines which have been deposited of the wild type coryneform bacteria, there can be mentioned *Corynebacterium glutamicum* ATCC 13032, *Corynebacterium acetoglutamicum* ATCC 15806 and also *Brevibacterium flavum* ATCC 14067. Examples of mutants or production strains which are suitable for producing L-serine are organisms from the group of *arthrobacter, pseudomonas, nocardia, methylobacterium, hyphomycrobium, alcaligenes* or *klebsiella*. The present invention will be characterized in greater detail based upon the aforementioned bacterial lines but, is not however limited thereto.

The term nucleic acid or nucleic acid fragment is to be understood, in accordance with the present invention, to refer to a polymer of RNA or DNA which is single-stranded or double-stranded and optionally can contain, natural, chemically synthesized, modified or artificial nucleotides. The term DNA polymer includes also genomic DNA, cDNA or mixtures thereof.

Under the term "allele", there is to be understood in accordance with the invention functional equivalents, namely, substantially identically effective nucleotide sequences. Functionally equivalent sequences are such sequences which in spite of different nucleotide sequences, for example resulting from the degeneration of the genetic code, nevertheless retain the desired functions. Functional equivalents encompass therefore naturally occurring variants of the herein described sequences as well as synthetic mucleotide sequences, for example those produced by chemical synthesis and optionally mucleotide sequences matched to the codon requirements of the host organism.

A functional equivalent will be understood to include especially also natural or synthetic mutations of originally isolated sequences which have the desired function. Mutations include substitutions, additions, deletions, replacements or insertions of one or more nucleotide residues. Included here are also so-called sense mutations which can give rise at the protein level, for example, to exchange of conserved amino acids which, however, do not lead to any basic change in the activity of the protein and thus are functionally neutral. These include also alterations in the nucleotide sequence which at the protein level affect the N-terminus of proteins without however significantly detracting from the function of the protein.

The nucleotide sequences encompassed by the present invention include also such nucleotide sequences as can be obtained by modification of the nucleotide sequences resulting in corresponding derivatives. The goal of such a modification can be, for example, the further localization of the coded sequence contained therein, or for example, also the insertion of further restriction enzyme cutting sites.

In addition, artificial DNA sequences can be the subject of the present invention as long as they, as described above, possess the desired characteristic. Such artificial DNA sequences can, for example, be those created by means of computer supported programs (molecular modelling) to produce the desired protein or selected by in vitro selection. Especially suitable are coded DNA sequences which have been modeled to produce a polypeptide sequence which can be obtained by the specific codon utilization of the root organism. The specific codon utilization can be readily determined by the skilled artisan in molecular genetic methods by computer evaluation of other previously known genes of the organism to be transformed.

The term "homologous sequences" is to be understood, in accordance with the invention, to refer to nucleotide sequences which are complementary to those of the invention and/or which hybridize with them. The term "hybridizing sequence" encompasses, according to the invention, substantially similar nucleotide sequences from the group of DNA or RNA which under stringent conditions known per se interact or bind with the aforementioned nucleotide sequences. In this category can be counted also those short nucleotide sequences with a length of for example 10 to 30 and preferably 12 to 15 nucleotides. These include according to the invention, among others, also so-called primers or probes.

The invention also includes the coded regions (structure genes) starting from (5'- or upstream) and/or subsequent (3'- or downstream) sequence regions. Especially included herein are sequence regions with a regulatory function. They can include the regions which influence transcription, RNA stability or RNA processing as well as translation. Examples for the encompassed regulatory sequences are among others, promoters, enhancers, operators, terminators or translation amplifiers.

The subject matter of the invention is in addition a gene structure containing at least one of the aforedescribed nucleotide sequences coding for a deregulated PDG as well as for the regulatory sequences operatively linked therewith and which control the expression of the coded sequences in the host cell.

The present invention further comprises a vector containing a nucleotide sequence of the aforedescribed type coding for a deregulated PDG or regulatory nucleotide sequences operatively linked therewith as well as additional nucleotide sequences for the selection of transformed host cells, for the replication within the host cell or the integration in the corresponding host cell genome. The vector according to the invention can additionally contain a gene structure of the aforedescribed type.

As vectors, those are suitable which can be replicated in coryneform bacteria like for example pZ1 (Menkel E, Thierbach G, Eggeling L, Sahm H., 1989, *Appl Environ Microbiol* 55(3): 684-688, pEKEx2 (Eikmanns et al., Gene 102: 93-98 (1991), pVWEx or pXMJ19. Other plasmid vectors can be used in the same way. This enumeration is not however limiting for the present invention.

Utilizing the nucleic acid sequence according to the invention corresponding probes or also primers can be synthesized and used for example to amplify and isolate analogous genes from other microorganisms, preferably coryneform bacteria, with the aid of the PCR technique.

The present invention also includes a probe for identifying and/or isolating genes coding for proteins participating in the biosynthesis of L-serine whereby these probes are produced starting from the nucleic acid sequence of the aforedescribed type and contain suitable markers for detection. The probes can be a partial segment of a sequence according to the invention, for example a conserved region which for example can have a length of 10 to 30 nucleotides, preferably 12 to 15 nucleotides, which can hybridize under strict conditions specifically with homologous nucleotide sequences. Numerous suitable markers are known from the literature. The skilled worker is advised to consult, among others, as examples, the Handbook of Gait: Oligonucleotide synthesis: a practical approach (XRL Press, Oxford, UK, 1984) and Newton and Graham: PCT (Spectrum Akadamischer Verlag, Heidelberg, Germany, 1994) or for example the Handbook "The DIG System Users Guide for Filter Hybridization" the firm Roche Diagnostics (Mannheim, Germany) or Liebl et al. (International Journal of Systematic Bacteriology (1991) 41: 255-260).

The subject of the present invention is also a deregulated PGD or a part thereof coded by a nucleic acid sequence according to the invention according to sequence ID No 1, 2, 3, 4 or 5 or a variation thereof of the previously described type. The present invention relates thus to a deregulated PGD with an amino acid sequence according to the SEQ ID No 7, 8, 9, 10 or 11 or a modified form of these polypeptide sequences or isoforms thereof or mixtures thereof. Especially suitable has been found to be 3-phosphoglycerate dehydrogenase with an amino acid sequence according to SEQ ID No 7.

The wild-type PGD is shown as SEQ ID NQ: 12.

It should be understood that isoforms are enzymes with the same or comparable substrate specificity and effectivity specificities which however have a different primary structure.

Modified forms are understood to be enzymes according to is the invention which, upon changes in the sequence, for example at the N-terminus of the polypeptide or in the region with conceived amino acids, retain the function of the enzyme without detriment. These variations can be in the form of amino acid replacements made by methods known per se.

The invention also encompasses polypeptides with the function of a deregulated PGD which has its amino acid sequence so altered that it has been desensitized and especially feed-back desensitized by comparison with compounds which are regulator effective and can for example regulate the activity of the metabolic end product L-serine.

The polypeptides according to the invention are characterized that they derive from *corynebacterium* preferably of the family *corynebacterium* or *brevibacterium* and especially preferably of the *Corynebacterium glutamicum* strain. Examples for the line cultures of wild type coryneform bacteria are the *Corynebacterium gluterricum* ATCC 13032, the *Corynebacterium acetoglutamicum* ATCC 15806 or *Brevibacterium flavum* ATCC 14067. Examples of the mutants or production line suitable for the production of L-serine are organisms from the group of *Arthrobacter, Pseudomonas, Nocardia, methylobacterium, Hypomycrobium, Alcaligenes* or *Klebsiella*. The present invention will be characterized in greater detail by the specification of the aforementioned bacteria lines but is not however limited thereby.

The subject of the present invention is in addition, the translation of at least one of the nucleic acid sequences according to the invention or a part thereof coded for a deregulated PGD, an allele homolog or derivative thereof in a host system. This translation of DNA in a host cell is effected in accordance with gene-technological methods. As a preferred process here is transformation and especially preferably the translation of DNA by electroporation.

A homologous host system has been found to be especially suitable. Under the designation of homologous host systems are to be understood microorganisms which belong to all of the families used. In accordance with the invention under this designation all coryneform bacteria according to the invention are to be understood in which nucleic acids derived from coryneform bacteria are incorporated. A nucleic acid translation carried out in accordance with this principle results in a transformed microorganism different from the corresponding untransformed microorganism in that it contains additional nucleic acids in accordance with the invention and correspondingly can be expressed. As an example of a suitable homologous host system, the bacterium *Corynebacterium glutamicum* and preferably the strain ATCC 13032.

As the culture medium depending upon the specific requirements, a complex medium like for example LB Medium (T. Maniatis, E. F. Fritsch and J. Sambrook, Molecular Cloning: A Laboratory Manual, Cold Spring Harbor Laboratory, Cold Spring Harbor, N.Y. 1989)) or also a Mineral salt medium like for example CGXII-Medium (Keilhauer, C. et al 1993, J. Bacteriol., 175:5593-5603) are suitable.

After corresponding cultivation, the bacterial suspension can be harvested and used for further investigation, for example, by transformation or isolation of the nucleic acid by conventional methods. This procedure can analogously be used also for other coryneform bacterial strains. In that case as the host system, bacteria of the *Corynebacterium* or *Brevibacterium* families are preferred. Within the *Corynebacterium* family, especially the *Corynebacterium glutamicom* species and within the *Brevibacterium* family, especially the *Brevibacterium flavum* species are preferred. The representatives of these families include those strains which have, from their properties been characterized as Wild Types.

Examples of suitable lines of this type are *Corynebacterium glutamicum* ATCC 13032, *Corynebacterium glutamicum* ATCC 19752, *Corynebacterium acetoglutamicum* ATCC 15806, *Corynebacterium acetogiutamicum* ATCC 15806, *Corynebacterium melassecola* ATCC 17965, *Corynebacterium thermoaminogenes* FERN BP-1539, *Brevibacterium flavum* ATCC 14067, *Brevibacterium lactofermentum* ATCC 13869 and *Brevibacterium divaricatum* ATCC 14020 can be mentioned.

In addition, the present invention also includes bacteria strains as host systems which are characterizable as L-serine producing mutants or amino acid production strains. These can be made, for example, starting from wild type lines by classical (chemical or physical) or gene technology methods. Examples of suitable lines of this type according to the invention are, among others, *Corynebacterium glutamicum* ATCC 21586, *Corynebacterium glutamicum* KY 10150, *Corynebacterium glutamicum* ATCC 13032ΔpanBC and *Brevibacterium ketoglutamicum* ATCC 21222.

In addition such production strains are suitable according to the invention which are known from microbial production methods to the artisan, like for example enterobacteria, bacillaceen or yeast types. The present invention is characterized in greater detail by these exemplary microorganisms but is not however limited thereby.

The present invention relates further to a genetically altered microorganism containing in replicatable form a nucleic acid of the aforedescribed type in accordance with the invention and which in comparison to the corresponding not genetically altered microorganism can be expressed in an amplified manner and/or with an increased copy number. The present invention also encompasses a genetically altered microorganism containing in replicatable form a gene structure or a vector of the aforedescribed type.

The present invention also has as its subject matter a genetically altered microorganism containing a polypeptide according to the invention with the function of a deregulated PGD of the aforedescribed type which, in comparison to the orresponding not genetically altered microorganism has a reduced feedback inhibition or no feedback inhibition by L-serine while maintaining the PGD activity. A genetically altered microorganism according to the invention is characterized further in that it is a coryneform bacterium, preferably of the *corynebacterium* or *Brevibacterium* families and especially preferably of the *Corynebacterium glutamicum* or *Brevibacterium flavum* species.

Basically genes can be amplified and then isolated by methods known per se like, for example, the polymerase chain reaction (PCR) with the aid of short synthetic nucleotide sequences (primers). The production of the primer used is effected generally based on known gene sequences utilizing homologies in conserved regions of the gene and/or taking into consideration the GC content of the DNA of the microorganism investigated.

A further procedure for isolating coding nucleotide sequences is the complementation of so-called defect mutants of the organism investigated which at least phenotypically show a function loss in the activity of the gene investigated or the corresponding protein. To be understood under "complementation" is the removal of the gene defect of the mutant and substantial reproduction of the original appearance prior to the mutagenesis which creates the functional gene or gene fragment from the microorganism investigated.

A classical mutagenesis process for producing defect mutants is for example the treatment of the bacteria cell with chemicals like, for example, N-Methyl-N-Nitro-N-Nitrosoguanidine or by UV irradiation. Such processes for triggering mutation are in general known and can among others be derived from Miller (A Short Course in Bacterial Genetics, A Laboratory Manual and Handbook for *Escherichia coli* and Related Bacteria (Cold Spring Harbor Laboratory Press, 1992)) or in the handbook "Manual of Methods for General Bacteriology" of the American Society for Bacteriology (Washington, D.C., USA, 1981).

The present invention relates also to a method for the microbial production of L-serine whereby at least one of the nucleic acids according to the invention, isolated from a coryneform bacterium, is translated in a host organism and is there expressed, whereby the gene expression and/or the activity of the corresponding coded polypeptide is increased by comparison with the corresponding nongenetically altered microorganism. This genetically altered microorganism is used for the microbial production of L-serin and the correspondingly formed L-serine is isolated from the culture medium.

To produce an enhanced gene expression (overexpression or superexpression), the copy number of the corresponding gene can be increased. In addition, the promotor region and/or regulation region and/or the ribosomal binding site which is located upstream of the structure gene, can be so altered correspondingly that the expression is effected at higher rates. Expression cassettes work in the same way and can be built in upstream of the structure gene. With inducible promoters it is possible in addition to increase the expression in the course of the fermentation L-serine production. Utilizing features for increasing the life span of the mRNA, the expression is also improved. The gene or gene construct can be integrated and amplified either in plasmids with different copy numbers or in chromosomes. Furthermore the activity of the enzyme itself can be increased or amplified by hindering the proteolysis of the enzyme protein. Alternatively, in addition, an overexpression of the gene involved can be achieved by varying the medium composition and culture conditions.

The artisan will find teachings thereof, in among others Martin et al. (Bio/Technology 5, 137-146 (1987)), in Guerrero et al. (Gene 138, 35-41 (1994)), Tsuchiya and Morinaga (BioRechnology 6, 428-430 (1988)), in Eikmanns et al (Gene 102, 93-98 (1991)), in the European Patent EPS 0 472 869, in U.S. Pat. No. 4,601,893, in Schwarzer and Pühler (Bio/Technology 9,84-87 (1991)), in Reinscheid et al. (Applied and Environmental Microbiology 60, 126-132 (1994)), in LaBarre et al. (Journal of Bacteriology 175, 1001-1007 (1993)), in the Patent application WO 96/15246, in malumbres et al (Gene 134, 15-24 (1993)), in the Japanese publication JP-A-10-229891, in Jensen and Hammer (Biotechnology and Bioengineering 58, 191-195 (1998)), in Makrides (Microbiological Reviews 60:512-538 (1996)) and in known textbooks of genetics and molecular biology.

The genetically modified microorganism produced in accordance with the invention can be made continuously or discontinuously in a batch process (set cultivation) or in a fed batch or a repeated fed batch process for the purpose of producing the L-serine. A collection of the known cultivation methods is described in the textbook of Chmiel (Bioprozesstechnik 1. Einfuhrung in die Bioverfahrenstechnik (Gustav Fischer Verlag, Stuttgart, 1991)) or in the textbook of Storhas (Bioreaktoren und periphere Einrichtungen (vieweg Verlag, Braunschweig/Wiesbaden, 1994).

The culture medium used must suffice in a suitable way to satisfy the requirements of the respective strain. Descriptions of culture media for various microorganisms are contained in the handbook "Manual of Methods for General Bacteriology" of the American Society for Bacteriology (Washington D.C., USA, 1981) as carbon sources, sugar and carbohydrates, like, for example, glucose, saccharose, lactose, fructose, maltose, molasses, starch and cellulose, oils and fats like for example soya oil, sunflower oil, peanut oil and coconut oil, fatty acids, like for example palmitic acids, stearic acids and linoleic acid, alcohols like for example glycerin and ethanol and organic acids like for example acetic acid can be used. These substances can be used individually or as mixtures. As nitrogen sources, organic nitrogen containing compounds like peptones, yeast extracts, meat extracts, malt extracts, maize spring water, soy bean meal and urea or inorganic compounds like ammonium sulfate, ammonium chloride, ammonium phosphate, ammonium carbonate and ammonium nitrate can be used. The nitrogen sources can be used individually or as mixtures.

As phosphorous sources, phosphoric acid, potassium dihydrogen phosphate, dicalcium hydrogen phosphate or corresponding sodium-containing salts can be used. The culture medium must in addition contain salts of metals like for example magnesium sulfate or iron sulfate which are necessary for the cultivation. Finally, essential growth elements like amino acids and vitamins are introduced in addition to the above-mentioned substances.

Appropriate precursors can in addition be added. The mentioned additives can be supplied to the culture in the form of a single introduction or can be fed during the cultivation. For pH control of the culture, basic compounds like sodium hydroxide, potassium hydroxide, ammonia or ammonia water or acid compounds like phosphoric acid or sulfuric acid can be introduced in a suitable way. To control the foam development, anti-foaming agents, like for example fatty acid polyglycol esters can be introduced. To maintain the stability of plasmids, appropriate selectively effective substances, for example antibiotics can be supplied to the medium. In order to maintain aerobic conditions, oxygen or oxygen-containing gas mixtures like for example air can be introduced into the culture. The temperature of the culture is normally between 20° C. to 45° C. and advantageously 25° C. to 40° C. The culturing is carried out for a period sufficient to produce a maximum of L-serine. This goal is normally reached within 10 hours to 160 hours.

The analysis of L-serine formation can be carried out by anion exchange chromatography with subsequent ninhydrin derivation, as described by Spackman et al. (Analytical Chemistry, 30, (1958), 1190) or can be carried out by reverse phase HPLC as described by Lindroth et al. (Analytical Chemistry (1979) 51: 1167-1174).

The microorganisms which are the subject of the present invention can make L-serine from glucose, saccharose, lactose, mannose, fructose, maltose, molasses, starch, cellulose or from glycerin and ethanol. It can use the previously described representatives of the coryneform bacteria class. A selection of results from the fermentation which has been given in Table 6.

This shows that the genetically altered microorganisms according to the invention give rise to a significantly improved L-serine production with respect to the corresponding nontransformed microorganisms (wild types) or the microorganisms which contain only the vector without the gene insert. In a special embodiment variant of the present invention it is shown that the overexpression of the homologous C-terminal-shortened serA gene in *C. glutamicum* ATCC 13032DpanBCpZ1serAΔ197 gives rise to at least a 40% increase in the L-serine accumulation in the medium by comparison to the control strain (Table 6). Through a corresponding overexpression of other genes which have a positive effect on the L-serine biosynthesis path, a still greater increase in the L-serine production can be expected.

Under amino acid production strains, in the sense of the present invention, *Corynebacterium glutamicum* strains or homologous microorganisms should be understood which are modified by classical and/or molecular genetic methods so that their metabolic flow is amplified in the direction of the biosynthesis of amino acids or their derivatives (metabolic engineering). For example, amino acid production strains can have one or more genes and/or corresponding enzymes which are modified at different and corresponding complex regulated key positions of the metabolic path (bottlenecks) or deregulated. The present invention encompasses therefore all already known amino acid production strains, preferably of the genus of *Corynebacteria* or homologous organisms. Furthermore, such production strains are encompassed in accordance with the invention which enable the skilled worker in the art in analogy with the knowledge from other organisms, especially enterobacteria, bacillaceen or yeast types, to develop commercial methods.

The Figures show exemplary plasmids which have been used as well as a comparison of the primary structure of the PGD and alleles of serA created by PCR.

The Figures show:

FIG. 1: A comparison of the primary structure of the 3-phosphoglycerate-dehydrogenase (PGD) from the different organisms; the scaling corresponding to the number of amino acids of the corynebacterial PGD; N=amino terminals; C=the carboxy terminals; the clear grey area marked region A indicates the nucleotide binding sites; the dark grey area marked region B shows the substrate binding site; the black marked region C shows the inhibitor binding site.

There are two further groups of 3-phosphoglycerate-dehydrogenases which, by way of example, are represented by *E. coli* (Tobey K. L. and Grant G. A., 1986, J. Biol. Chem., 261: 12179-12183) and *Thermotoga maritima* (Gene Bank Accession Number AE000512). In this connection the protein of the hyperthermophilic bacterium *T. maritima* with a length of 327 amino acids is the shortest while the 3-phosphoglycerate-dehydrogenase from *E. coli* with 410 amino acids has an intermediate length.

Figure 2:
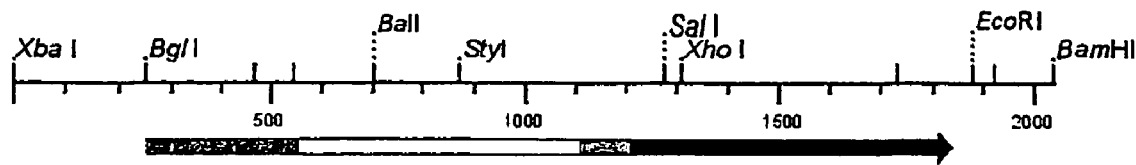
Figure 2:
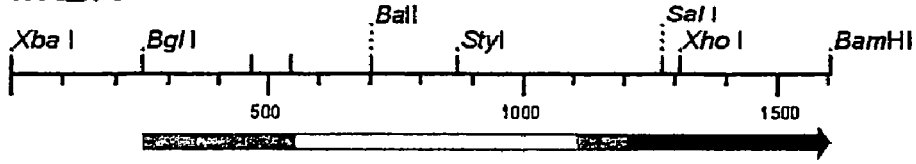
Figure 2:
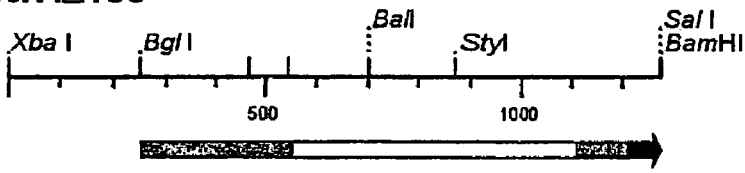
Figure 2:
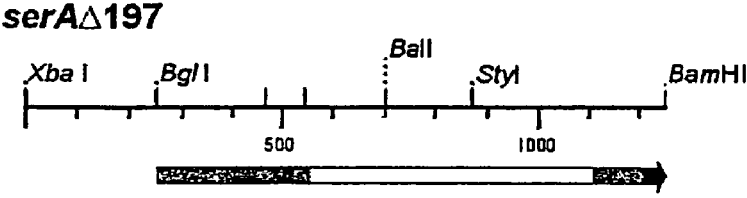
Figure 2:
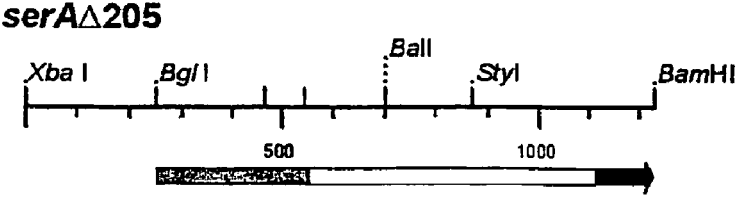
Figure 2:
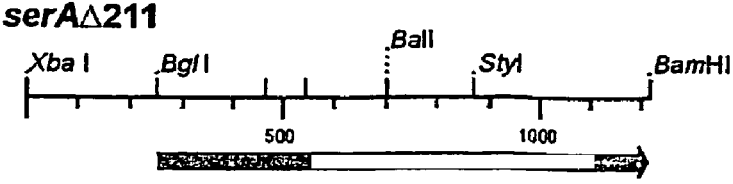

FIG. 2: an overview of the allele of serA made by means of PCR and which codes for the deregulated PGD shortened at the C terminal. Illustrated is the serA gene region of the wild type and the deletion construct according to the invention. The light, dark and black marked regions correspond to the definitions as in FIG. 1.

Figure 3:
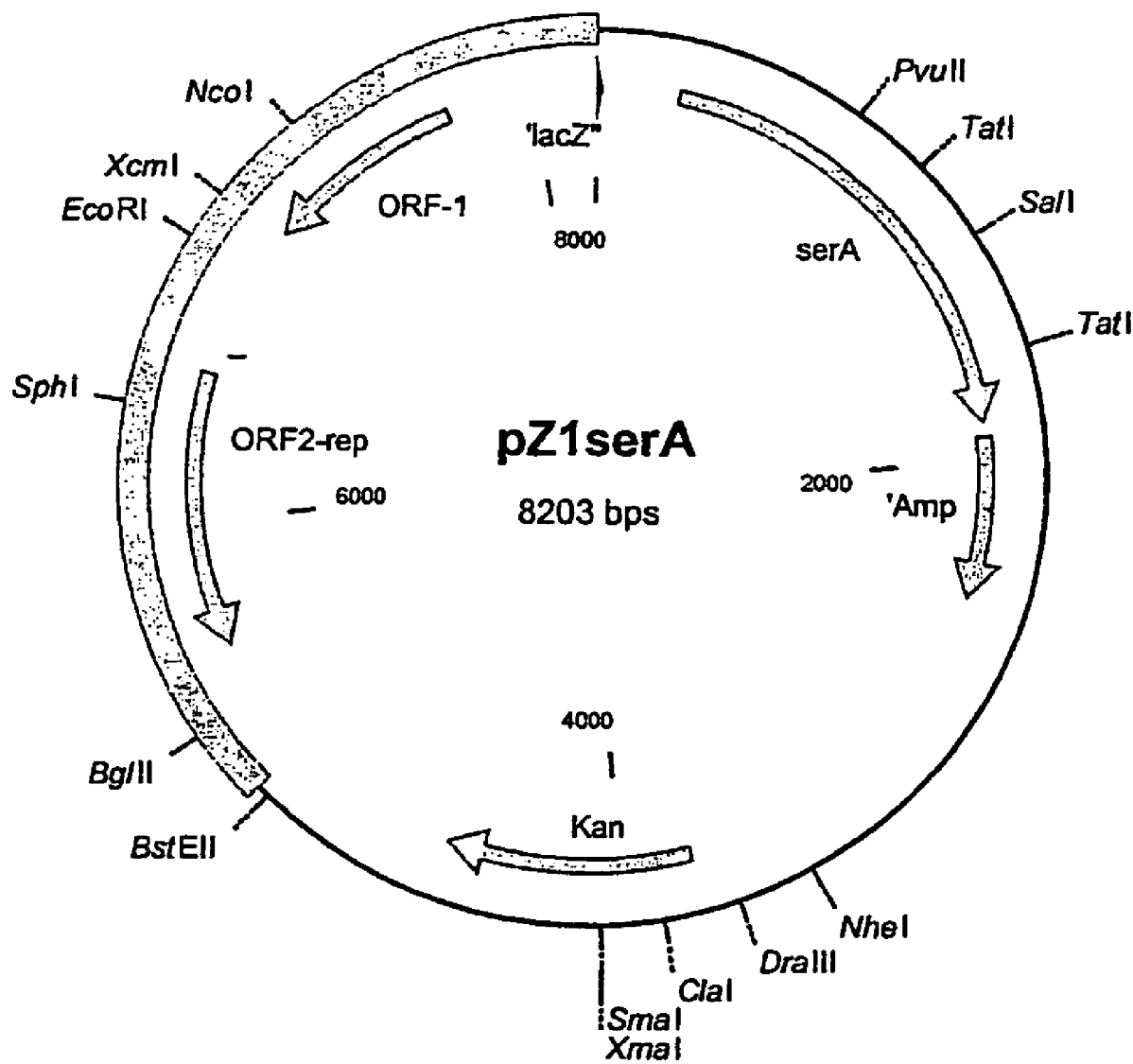
Figure 4:
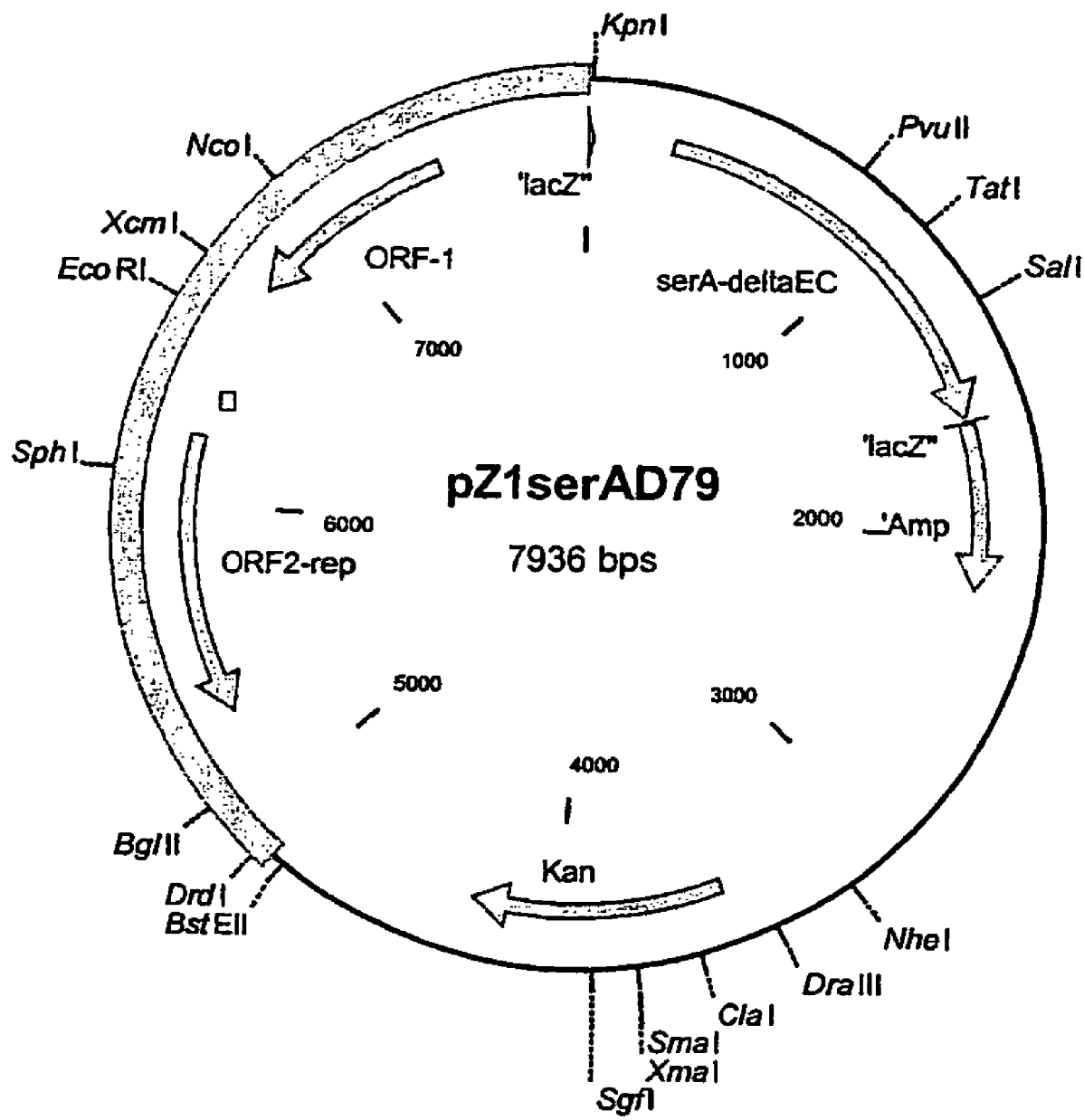
Figure 5:
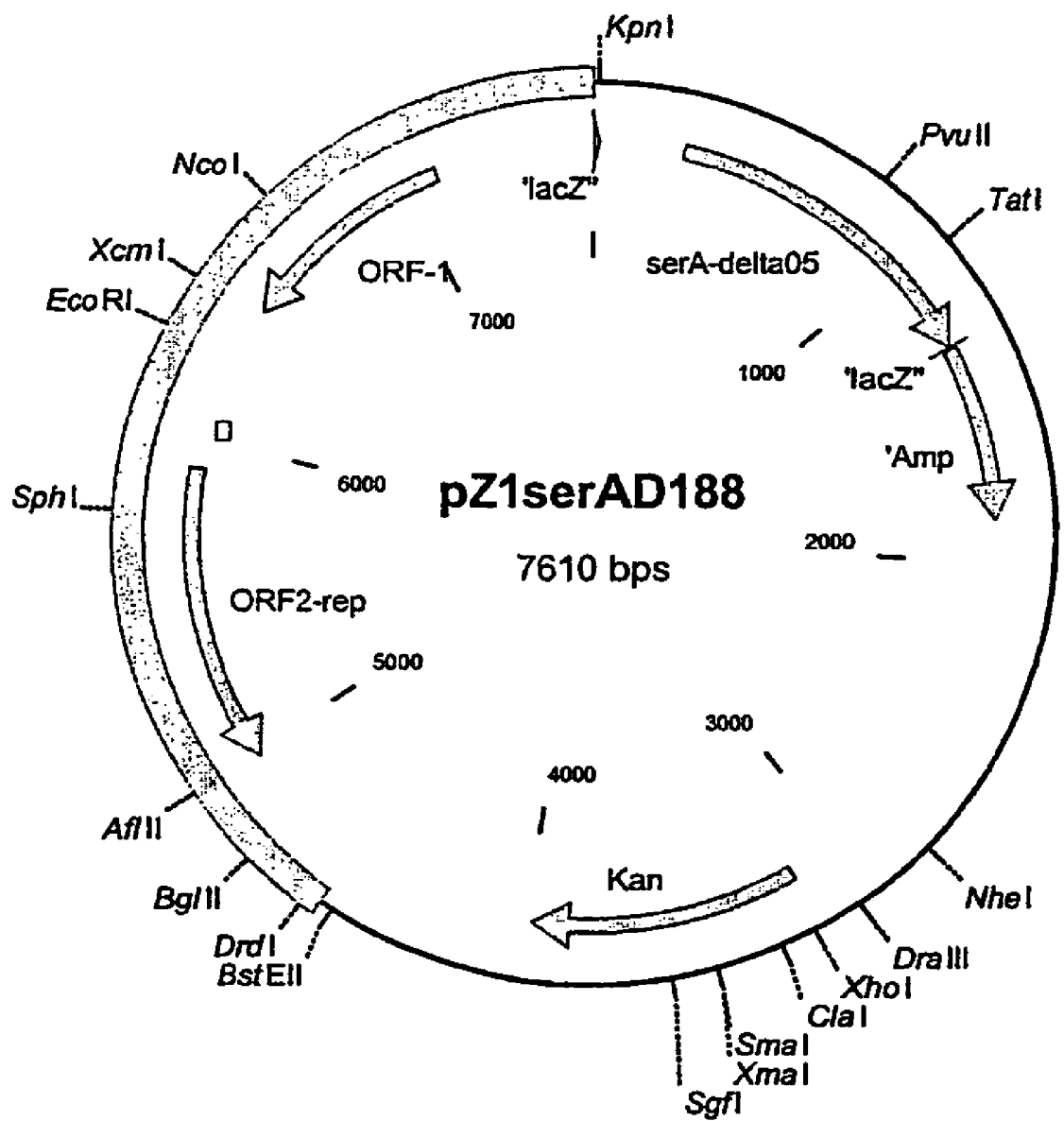
Figure 6:
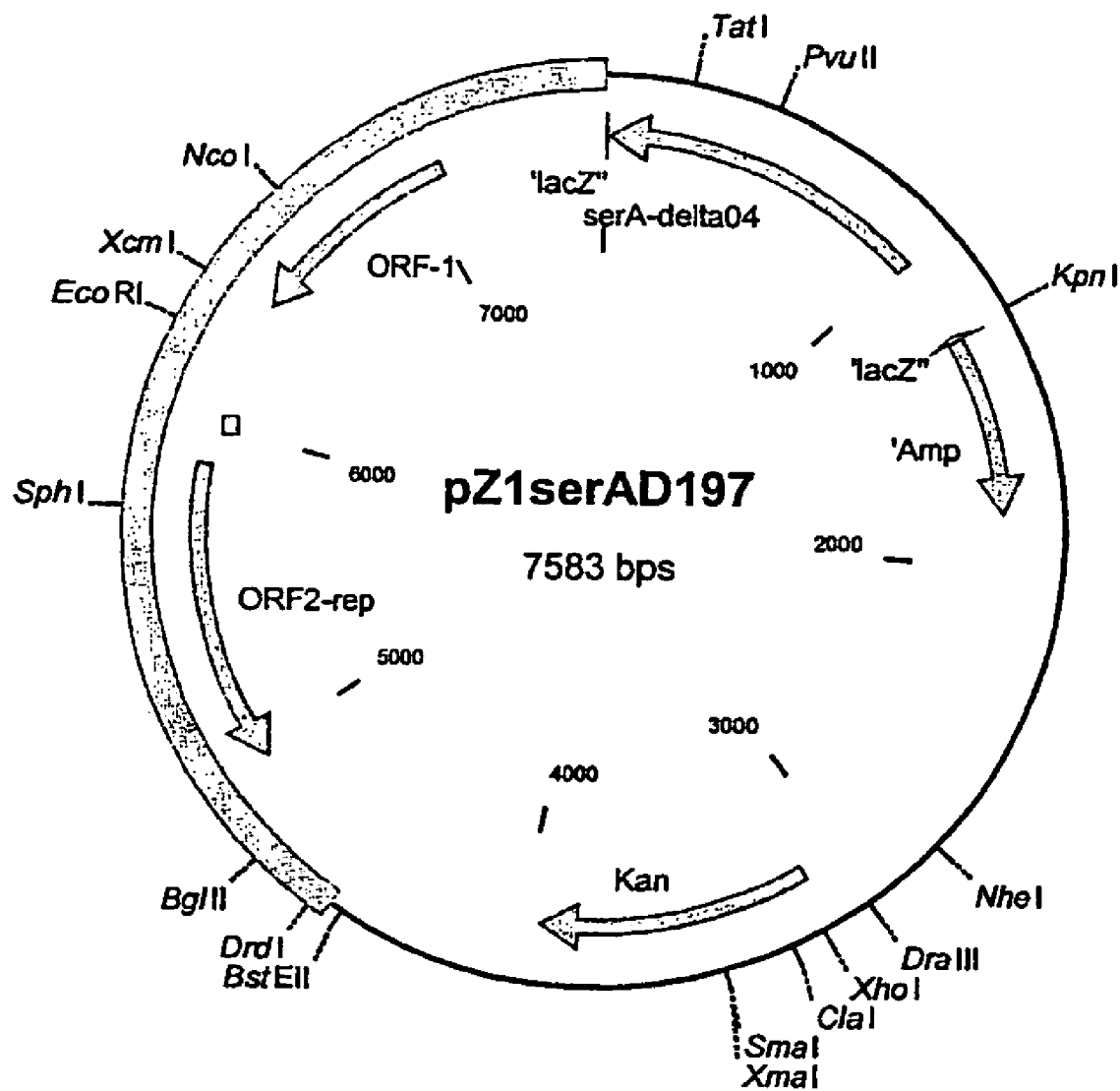
Figure 7:
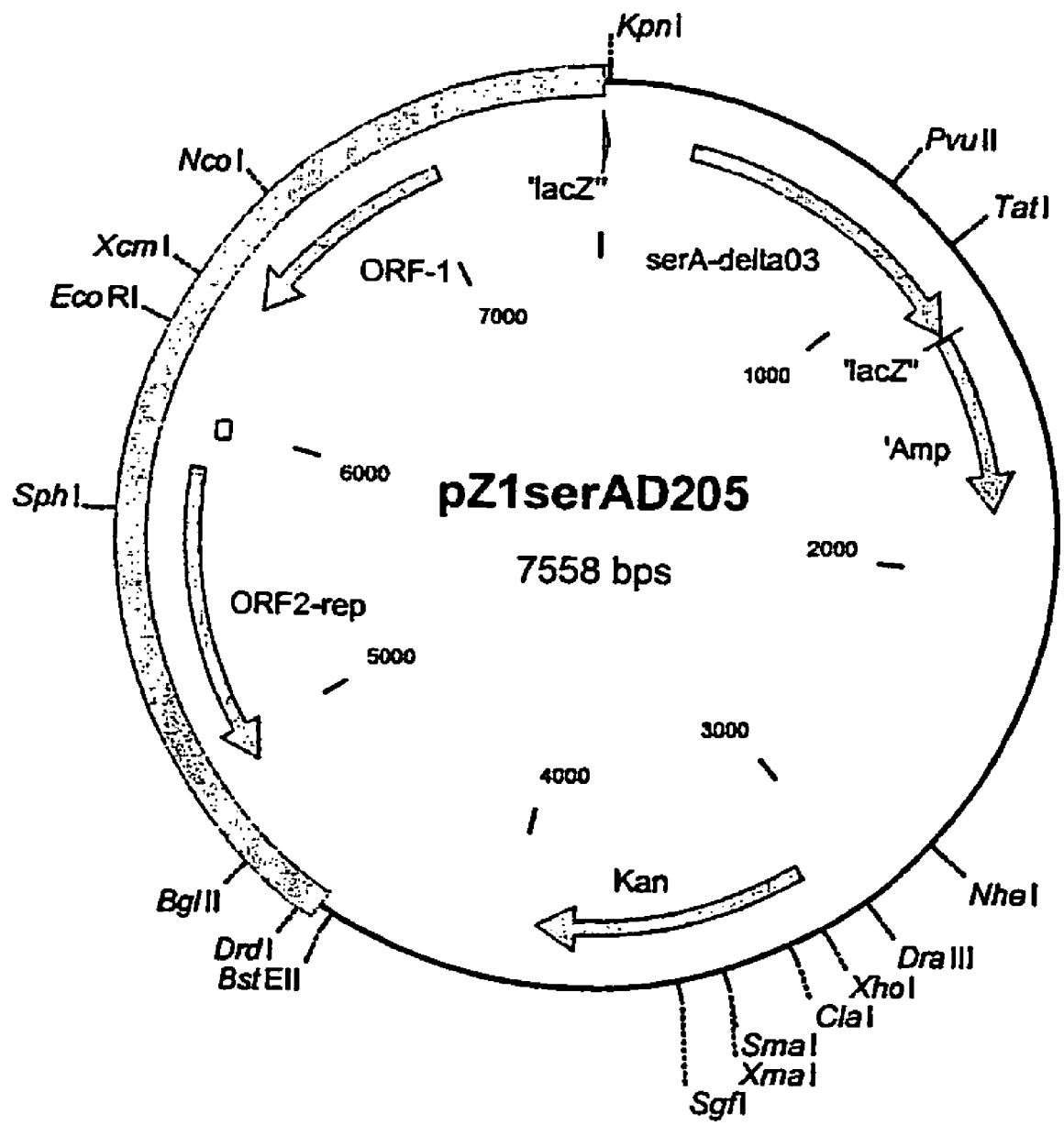

FIG. 3: Plasmid vector pZ1serA
FIG. 4: Plasmid vector pZ1serAΔ79
FIG. 5: Plasmid vector pZ1serAΔ188
FIG. 6: Plasmid vector pZ1serAΔ197
FIG. 7: Plasmid vector pZ1serAΔ205
FIG. 8: Plasmid vector pZ1serAΔ211

Exemplary Embodiments

1. Targeted Deregulation of the 3-Phosphoglycerate Dehydrogenase of *C. glutamicum* a) Computer Supported Amino Acid Sequence—Comparison of the 3-phosphoglycerate-dehydrogenase of *corynebacterium glutamicum* with 3-phosphoglycerate-Dehydrogenase from Other Organisms Initially a strategy for the construction of a deregulated 3-phosphoglycerate-dehydrogenase was developed. The sequence of the serA gene, which coded for the 3-phosphoglycerate-dehydrogenase of *C. glutamicum*, from the patent data bank was used Nakagawa, S., Mizogukchi, H., Ando, S., Hayashi, M., Ochiai, K., Yokoi, H., Tateishi, N., Senoh, A., Ikeda, M. and Ozaki, A. Patent: EP 1108790-A 7064 20 Jun. 2001; KYOWA HAKKO KOGYO CO., LTD. (JP); Pompejus, M., Kroeger, B., Schroeder, H., Zelder, O. and Haberhauer, G. Patent: WO 0100843-A 167 04-JAN 2001; BASF AKTIENGESELLSCHAFT (DE)).

The polypeptide chain derived from the sera gene (SEQ ID No. 12) of *Corynebacterium glutamicum* was compared with the corresponding 3-phosphoglycerate-dehydrogenase from the data bank (gene bank). It showed that the 3-phosphoglycerate-dehydrogenase from the *C. glutamicum* like that from *Mycobacterium tuberculosis* (gene bank accession No. AL123456) and several other bacteria *Bacillus subtilis* (Sorokin, A., Azevedo, V., Zuimstein, E., Galleron, N., Ehrlich, S. D. and Serror, P., Microbiology 142 (Pt 8), 2005-2016 (1996)) and *Aquifex aeolicus* (GenBank-Accession-Number AE000657) with 500 amino acids is unusually long. In this group of enzymes are counted also the 3-phosphoglycerate-dehydrogenase from animals like rats (Achouri Y., Rider N. H., Van Schaftingen E. and Robbi M., 1997, Biochem J., 323:365-370) and Mensch (Cho H N, Jun Dy, Bae M A, Ahn J D, Kim Y H., 2000, Gene 245(1):193-201) as well as plants (z. B. *Arabidopsis thaliana*; Ho CL, Saito K., 2001, Amino Acids. 20(3):243-59).

The analysis of the x-ray structure of the *E. coli* enzyme indicated that it is comprised of three functional domains: a nucleotide binding domain (amino acids 108 to 294) for the binding of NAD/H, a two part substrate binding domain (amino acids 7-107 and 295-336) to which the 3-phosphoglycerate binds as well as a C-terminal regulatory domain (amino acids 337-410) which accounts for the allosteric binding of the L-serine (Schuller D J, Grant G A, Banaszak L F., 1995, Nature Struct. Biol. Vol 2 1:69-76).

The amino acid sequence comparison of the 3-phosphoglycerate-dehydrogenase types indicated that they differed substantially in the length of the C-terminal regulatory domain (FIG. 1).

A cluster analysis of the 3-phosphoglycerate-dehydrogenase, which was known from the completely sequenced genome, indicated that in spite of the difference in the C-terminus, all of these proteins were part of a family of orthologs, that is that they had a common evolutive origin although they had developed differently in different species.

b) Construction of Alleles of the serA-Gene of *C. glutamicum* by Means of PCR which Code for C-terminal-shortened 3phosphoglycerate-dehydrogenase proteins Five different mutations of the 3-phosphoglycerate-dehydrogenase of *C. glutamicum* were produced which had deletions of different lengths at the C terminal (FIG. 2). The construction of the deletion mutant is carried out in the same manner as the isolation of the wild type serA- gene by means of PCR. For this purpose, a PCR primer (serA-f: 5'-TCTA-GAGCCGGAGACGTGAATAAAAT-3 ') {SEQ ID NO: 13} is produced, the homologue being to a region 240 bp prior to the start codon of the gene to encompass the entire promoter region. This primer is used for all constructs and carries at the 3' end a cutting site for the restriction enzyme XbaI. For the amplification of the complete serA gene, a second reverse complementary primer is selected which lies 199 bp behind the stop codon and carries a BamHI restriction site (serA-r: 5' GGATCCGACTGGTGAGGGTCAAGTCC-3') [SEQ ID NO: 14].

The expected PCR product has a length of 2040 bp. To produce the deletion, a reverse complementary primer is selected which lies in the gene region and carries a restriction site for BAMHI. The primer serAΔ211-r (5'-GGATCCT-TAACCGGAAACGTTCACAGC-3') {SEQ ID NO: 15] lies 956 bp behind the start codon so that a PCR product with a length of 1196 bp results. The last 211 amino acids of the 3-phosphoglycerate-dehydrogenase are cut off. The deletion lies generally in the region of the assumed transition from the substrate binding domain to the regulatory domain (compare FIGS. 1 and 2). The primer serAΔ205-r (5'-GGATCCT-TACTCTTCGCCCACGCGACC-3') {SEQ ID NO: 16] lies 974 bp behind the start codon and the expected PCR product has a length of 1214 bp. The C terminal deletion in this case amounts to 204 amino acids and the protein terminates behind the amino acid glutamate at position 325. The undirected exchange of this amino acid to lysine produces in *C. glutamicum* a deregulation of the 3-phosphoglycerate-dehydrogenase (EP 0 931 833). Both deletions lie in a region in which the deletion (Δ209 amino acids) of rat protein has been produced. Achouri Y., Rider M. H., Van Schaftingen E. and Robbi M., 1997, Biochem J., 323-365-370. Both primers serAΔ197-r (5' -GGATACCTTAAGCCAGAATCCATCCA-CACAG-3') [SEQ ID NO: 17] and serAΔ188-r (5'-GGATC-CTTACTTGCCAGCAAGAAAAGACC-3') [SEQ ID NO: 18] lie 998 bp or 1025 bp behind the ATG and find themselves upstream from the transition from the substrate binding domain to the regulatory domain in *E. coli*. The polypeptide chain produced from the DNA fragment expected from the PCR is shorter by 197 or 188 corresponding amino acids than the full 3-phosphoglycerate-dehydrogenase. The shortest deletion is produced by the primer serAΔ79-r (5'-GGATC-CTTAATCCAGGCCACGGCCATT-3') [SEQ ID NO: 19] and cuts out the region of 79 amino acids which has the greatest similarity to the regulatory domain of *E. coli*. In addition in all of the reverse complementary primers, which give rise to a shortened protein, behind the restriction site, the stop code TAA is introduced.

The preceding seven primers have been assigned the respective designations: SEQ ID No. 13, SEQ ID No. 14, SEQ ID No. 15, SEQ ID No. 16, SEQ ID No. 17, SEQ ID No. 18 and SEQ ID No. 19.

The PCR reaction is carried out over 30 cycles in the presence of 200 μM deoxynucleotide-triphosphates (dATP, dCTP, dGTkP, in an amount of 1 μM of the corresponding oligonucleotides, 100 ng chromosomal AND from *corynebacterium glutamicum* ATCC13032, 1/10 volumes of 10 fold reaction buffers and 2.6 units of heat stabilized Tag-/Pwo-DNA-polymerase mixture (Expand High Fidelity PCR System of the Firm Roche Diagnostics, Mannheim, Germany) in a thermocycle (PTC-100 MJ Research, Inc., Watertown, USA) under the following conditions: 94° C. for 60 seconds, 50° C. for 90 seconds and 72° C. for 2 minutes.

Following the PCR reaction, the obtained DNA fragments are isolated with the QIAExII gel extraction kit (Qiagen) in accordance with the conditions of the manufacturer, from 0.8% agarose gel and cloned blunt-end with the aid of the Sure Clone Kits (Amersham Pharmacia Biotech) in the SmaI restriction site of the vector pUC18. The plasmid is tested by restriction mapping for accuracy. This cloning was carried out in the *Escherichia coli* strain DH5αmcr (Grant et al., Proceedings of the National Academy of Sciences of the United States of America USA (1990) 87: 4645-4649).

Figure 8:
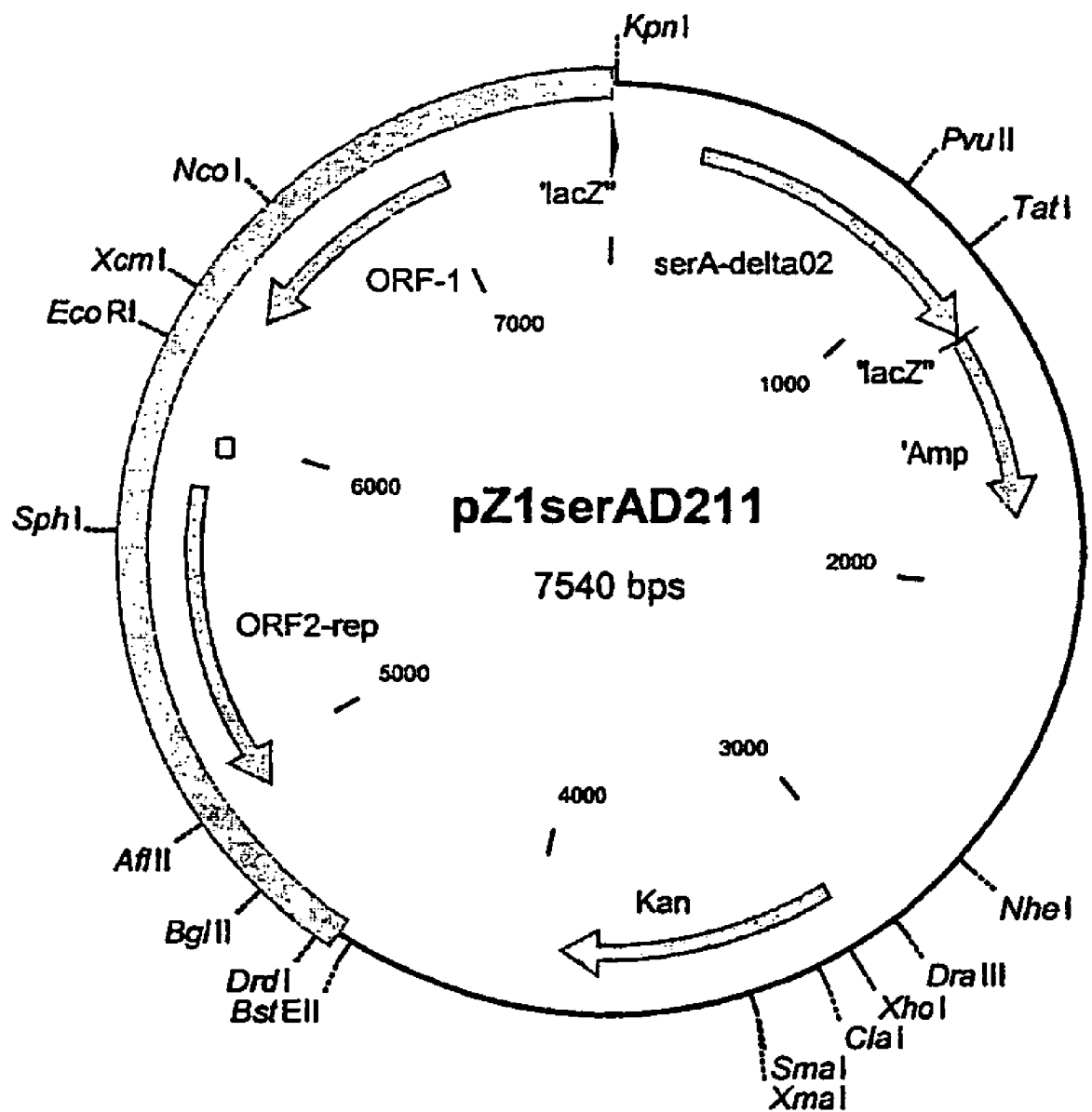

Then the serA-gene and serA-deletion construct were cloned in the *E. coli/C glutamicum* swing vector pZ1 (Henkel E. Thierbach G. Eggeling L. Sahm H., 1989, *Appl Environ Microbiol* 55(3): 684-688. The vector enabled the kanamycin resistance. The inserts of the deletion construct were respectively cut out by the restriction enzymes EcoRI and BamHI from the pUC18 vector. The overhanging DNA ends were filled by means of a Klenow treatment and the fragments were ligated blunt end in the ScaI-cleaved vector pZ1. The so obtained constructs were named pZiserA (FIG. 3), pziserAΔ79 (FIG. 4), pZiserAΔ188 (FIG. 5), pZiserAΔ197 (FIG. 6), pZiserAΔ205 (FIG. 7) and pZiserAΔ211 (FIG. 8).

2. Overexpression of the Wild Type serA-Gene and the Foreshortened serA-Allele in *C. glutamicum*

The plasmids pziserA, pZiserAΔ79, pZiserAΔ188), pZiserAΔ197, pZiserAΔ205 and pZiserAΔ211 were introduced by electroporation individually into *C. glutamicum*. As a control, the media plasmid pZ1 was also electroporated into *C. glutamicum* ATCC 13032. The thus obtained strains 13032pZ1, 13032pZ1serA, 13032pZiserAΔ79, 13032pZiserAΔ188, 13032pZiserAΔ197, 13032pZiserAΔ205 and 13032pZiserAΔ211 were analyzed for overexpression of the 3-phosphoglycerate-dehydrogenase by means of is the 3-phosphoglycerate-dehydrogenase enzyme test. For this purpose the six strains were activated in complex medium (CgIII=2.5 g NaCl, 10 g bacto-peptone, 10 g bacto-yeast extract, pH 7.4 with 2% glucose) and the minimal medium CGXII and each was separately seeded from the preculture. The medium was identical with the medium CGXII described by Keilhauer et al (Journal of Bacteriology (1993) 175: 5593-5603) but containing additionally 25 μg/mL of kanamycin. The composition of the medium described by Keilhauer is given in Table 1.

TABLE 1

Composition of the Medium CGXII

| Components | Concentration |
| --- | --- |
| (HN$_4$)$_2$SO$_4$ | 20 g/L |
| Urea | 5 g/L |
| KH$_2$PO$_4$ | 1 g/L |
| K$_2$HPO$_4$ | 1 g/L |
| MgSo$_4$ × 7H$_2$O | 0.25 g/L |
| 3-Morpholinopropansulfanic acid | 42 g/L |
| CaCl$_2$ | 10 mg/L |
| FeSo$_4$ × 7H$_2$O | 10 mg/L |
| MnSO$_4$ × H$_2$O | 10 mg/L |
| ZnSO$_4$ × 7H$_2$O | 1 mg/L |
| CuSO$_4$ | 0.2 mg/L |
| NiCl$_2$ × 6H$_2$O | 0.02 mg/L |

TABLE 1-continued

Composition of the Medium CGXII

| Components | Concentration |
| --- | --- |
| Biotin | 0.2 mg/L |
| Glucose | 40 g/L |
| Protocatechuic acid | 30 mg/L |

The cells were harvested in the exponential growth phase at OD$_{600}$ of 5 to 8 and washed twice in 100 mM Tris-HCl, pH 7.5. The cell pellets were then frozen at −20° C. until disintegration. The frozen cell pellets were moisturized on ice and resuspended with 2 ml cold Tris-HCl pH 7.5/10% glycerine in a Brenson sonifier for 10 minutes. Then the cell fragments were separated by centrifugation at 13000 rpm and 4° C. in a Sigma −202 MK centrifuge. The thus obtained supernatant is desalted as a raw extract initially on a PD-10 column using the conditions set by the manufacturer (Amersham Pharmacia Biotech) and then immediately subjected to enzyme measurement. The enzyme test relied upon the photometric detection of the formation of NADH in the reaction of 3-phosphoglycerate and NAD to NADH. The test composition is shown in Table 2.

TABLE 2

Components of the Test composition in Determination of the 3-Phosphosphoglycerate-Dehydrogenase Activity

|  | Original Solution | End Concentration |
| --- | --- | --- |
| Tris-HCl: pH 8.8 | 500 mM | 100 mM |
| Dithiothreite | 100 mM | 1 mM |
| EDTA | 500 mM | 5 mM |
| Hydrazine | 250 mM | 10 mM |
| NAD | 20 mg/ml | 2 mg/ml |
| RE | ca. 2 mg/ml | ca. 200 μg protein |
| 3-phosphoglycerate | 150 mM | 15 mM |

With these test results a specific activity of about 150 mU/mg protein can be determined for the wild-type 3-phosphoglycerate-dehydrogenase activity. It was found that the overexpression of the complete serA gene gave about a 16-fold increase in the specific 3-phosphoglycerate-dehydrogenase activity. The construct serAΔ197 gives a 10-fold overexpression with respect to the wild type protein. The constructs serAΔ188 and serAΔ205 allow a 3 to 3.4 fold overexpression whereas for the constructs serAΔ205 and serAΔ79 only a 1.2 to 1.5 fold overexpression is possible. Thus it has been shown that through deletion of the C-terminal 197 amino acids of 3-phosphoglycerate-dehydrogenase from *C. glutamicum* produced mutant serAΔ197 is functional and has more than 60% of the wild type activity.

In Table 3 the results have been collected.

TABLE 3

Overexpression of the serA gene and the C-terminal foreshortened serA allele.

| Line | Specific PGD Activity [U/mg Protein] | Factor of Overexpression |
| --- | --- | --- |
| 13032pZ1 | 130 | 1.0 |
| 13032pZ1 serA | 2140 | 16.5 |
| 13032pZ1 serAΔ79 | 190 | 1.5 |
| 13032pZ1 serAΔ188 | 440 | 3.4 |
| 13032pZ1 serAΔ197 | 1320 | 1.5 |

TABLE 3-continued

Overexpression of the serA gene and the C-terminal foreshortened serA allele.

| Line | Specific PGD Activity [U/mg Protein] | Factor of Overexpression |
|---|---|---|
| 13032pZ1 serAΔ205 | 390 | 3.0 |
| 13032pZ1 serAΔ211 | 150 | 1.2 |

*The 3-phosphoglycerate-dehydrogenase activity in line 13032pZ1 was normalized to 1.0.

3. Investigation of the Inhibition of the Wild Type 3-Phosphoglycerate-Dehydrogenase of *C. glutamicum* and the C-terminal Foreshortened Mutant serAΔ197 by L-Serine In the following tests were made whether the C-terminus foreshortened mutant serAΔ197 was no longer blocked by L-serine. For that purpose initially the inhibition of the 3-phosphoglycerate-dehydrogenase of the wild type was investigated in cell-free extracts of *C. glutamicum* by L-serine based upon the above described enzyme tests. For that purpose to the test bath were added 1, 5 and 10 mM L-serine and were incubated for 5 minutes at 30° C. The reaction was then started by the addition of 15 mM 3-phosphoglycerate-dehydrogenase. The incubation was necessary in order to be able to detect an inhibition (Table 4). This time dependency of the L-serine inhibition which required several minutes of incubation before a constant level of inhibition was reached has also been described for other 3-phosphoglycerate-dehydrogenase, for example for the purified enzyme of *B. subtilis* (Saski R. and Pitzer L., 1975, Eur. J. Biochem., 51:415-427).

TABLE 4

Inhibition of the Wild Type 3-Phosphoglycerate-Dehydrogenase of *C. glutamicum* by L-Serine

| L-Serine [mM] | Relative 3-Phosphoglycerate-Dehydrogenase Activity [%] | |
|---|---|---|
| | Without Incubation | 5 Minute Incubation at 30° C. |
| 0 | 100* | 100* |
| 1 | 106 | 96 |
| 5 | 112 | 82 |
| 10 | 104 | 56 |

*The activity of the 3-phosphoglycerate-dehydrogenase was set at 100% addition of L-serine.

Building on these results, the L-serine inhibition 3-phosphoglycerate-dehydrogenase in the 13032pZ1serA and 13032pZ1serAΔ197 lines was explored. It was found that indeed, the C-terminal foreshortened 3-phosphoglycerate-dehydrogenase mutant no longer was significantly limited by L-serine (Table 5).

TABLE 5

Inhibition of the Overexpressed 3-phosphoglycerate-dehydrogenase by L-serine in the strains 13032pZ1serA and 13032pZ1serAΔ197

| L-Serine [mM] | Relative 3-Phosphoglycerate-Dehydrogenase Activity [%]** | |
|---|---|---|
| | 13032pZ1serA | 13032pZ1serAΔ197 |
| 0 | 100* | 100* |
| 10 | 34 | 95 |

*The activity of the 3-phosphoglycerate-dehydrogenase was set at 100% addition of L-serine.
**Determination of the activity after 5 minutes of incubation at 30° C. with and without L-serine.

Thus it was found that the generation of a deregulated 3-phosphoglycerate-dehydrogenase mutant in a targeted way by deletion of the C-terminus of the 3-phosphoglycerate-dehydrogenase from *C. glutamicum* was successful.

4. Increased Accumulation of L-Serine by Overexpression of the Gene for the Deregulated 3-Phosphoglycerate-Dehydrogenase (serAΔ197)

For analysis of the L-serine production by the line with deregulated 3-phosphoglycerate-dehydrogenase, the plasmids pZ1, pZ1serA and pZ1serAΔ197 in the strain *Corynebacterium glutamicum* 13032ΔpanBC was transformed (E. Radmacher, A. Vaitsikova, U. Burger, K. Krumbach, H. Sahm, L. Eggeling, 2002, Appl. Environ. Microbiol. (Publication in preparation)). This line is auxotrophic as to pantothenae through the deletion of the pantothenate by synthesis genes panB and panC and is distinguished in that under pantothenate limitation, it produces because of an increased accumulation of pyruvate, about 50 mM alanine and 8 mm valine. In addition, the strain forms about 100 µM L-serine and is suitable as a starting strain for the construction of a L-serine producing strain. The strain with the plasmid pZ1serA was deposited in accordance with the Budapest agreement on 11 Apr. 2002 with the DSMZ under the DSM No. 14922.

To explore the L-serine production the three lines were cultured in complex medium (CgIII with 2% glucose and with 50 µg/1 kanamycin) and the fermentation medium CGXII (J Bacteriol (1993) 175: 5595-5603) each seeded from the pre-culture. The medium contained additional 50 µg/1 kanamycin and 1 µM pantothenate. Two independent fermentations were carried out. After cultivation for is 24 or 25 hours at 30° C. on a rotation shaker operating at 120 rpm, the L-serine quantity accumulated in the medium was determined. The determination of the amino acid concentration was effected by high pressure liquid chromatography. (J Chromat (1983) 266: 471-482). The results of the fermentation are given in Table 6 and show that even the overexpression of the wild type serA gene can give rise to about 10% increase in the L-serine accumulation in the medium. The overexpression of the deregulated 3-phosphoglycerate-dehydrogenase produces by comparison an increase of up to 40% with respect to the control line which only contained the empty plasmid. Thus the use of the constructed and described gene for the deregulated L-serine biosynthesis enzyme 3-phosphoglycerate-dehydrogenase supported a process which significantly improved the L-serine formation.

TABLE 6

Accumulation of L-Serine in the Culture Supernatant of *Corynebacterium glutamicum* 13032ΔpanBC after Expression of Gene serA or serAΔ197

| Line | t [h] | TG [mg/ml] | L-Serine [µM] | L-Serine/TG [mg/g] |
|---|---|---|---|---|
| 13032DpanBCpZ1 | 24 | 18.3 | 164 | 0.9 |
| 13032DpanBCpZ1serA | 24 | 14.7 | 163 | 1.2 |
| 13032DpanBCpZ1serAΔ197 | 24 | 16.5 | 199 | 1.3 |

*TG = Cell dry weight

The invention claimed is:

1. An isolated nucleic acid consisting of SEQ ID NO: 1 where said sequence encodes a deregulated 3-phosphoglycerate dehydrogenase, which in comparison to a wild type 3-phosphoglycerate dehydrogenase has reduced feedback inhibition by L-serine where said nucleic acid is a fragment of an SerA gene.

2. An isolated nucleic acid consisting of SEQ ID NO: 2 where said sequence encodes a deregulated 3-phosphoglycerate dehydrogenase, which in comparison to a wild type 3-phosphoglycerate dehydrogenase has reduced feedback inhibition by L-serine where said nucleic acid is a fraqment of an SerA gene.

3. An isolated nucleic acid consisting of SEQ ID NO: 3 where said sequence encodes a deregulated 3-phosphoglycerate dehydrogenase, which in comparison to a wild type 3-phosphoglycerate dehydrogenase has reduced feedback inhibition by L-serine where said nucleic acid is a fraqment of an SerA gene.

4. An isolated nucleic acid consisting of SEQ ID NO: 4 where said sequence encodes a deregulated 3-phosphoglycerate dehydrogenase, which in comparison to a wild type 3-phosphoglycerate dehydrogenase has reduced feedback inhibition by L-serine where said nucleic acid is a fraqment of an SerA gene.

5. An isolated nucleic acid consisting of SEQ ID NO: 5 where said sequence encodes a deregulated 3-phosphoglycerate dehydrogenase, which in comparison to a wild type 3-phosphoglycerate dehydrogenase has reduced feedback inhibition by L-serine where said nucleic acid is a fraqment of an SerA gene.

6. An isolated nucleic acid according to claim 1, claim 2, claim 3, claim 4 or claim 5 isolated from coryneform bacteria.

7. An isolated nucleic acid according to claim 1, claim 2, claim 3, claim 4 or claim 5 isolated from *Corynebacterium* or *Brevibacterium*.

8. An isolated nucleic acid according to claim 1, claim 2, claim 3, claim 4 or claim 5 isolated from *Corynebacterium glutamicum* or *Brevibacterium flavum*.

9. The recombinant nucleic acid sequence of claim 1, claim 2, claim 3, claim 4 or claim 5 further comprising the 3-phosphoglycerate dehydrogenase regulatory sequence operably linked therewith.

10. An expression vector containing a recombinant nucleic acid sequence according to claim 9 as well as additional nucleotide sequence for selection, replication in a host cell or for integration in a host cell genome.

11. A mutant deregulated 3-phosphoglycerate dehydrogenase where said mutant 3-phosphoglycerate dehydrogenase is expressed from a nucleic acid consisting of SEQ ID NO: 1, SEQ ID NO: 2, SEQ ID NO: 3, SEQ ID NO: 4 or SEQ ID NO: 5 that encode the amino acid sequence of SEQ ID NO: 7, SEQ ID NO: 8, SEQ ID NO: 9, SEQ ID NO: 10 or SEQ ID NO: 11 respectively and where said mutant deregulated 3-phosphoglycerate-dehydrogenase has a reduced feedback inhibition by L-serine compared to the wild type 3-phosphoglycerate dehydrogenase.

12. A mutant deregulated 3-phosphoglycerate-dehydrogenase, which in comparison to a wild type 3-phosphoglycerate dehydrogenase has reduced feedback inhibition by L-serine according to claim 11 with an amino acid sequence consisting of SEQ ID No. 7.

13. A mutant deregulated 3-phosphoglycerate-dehydrogenase, which in comparison to a wild type 3-phosphoglycerate dehydrogenase has reduced feedback inhibition by L-serine according to claim 11 with an amino acid sequence consisting of SEQ ID No. 8.

14. A mutant deregulated 3-phosphoglycerate-dehydrogenase, which in comparison to a wild type 3-phosphoglycerate dehydrogenase has reduced feedback inhibition by L-serine according to claim 11 with an amino acid sequence consisting of SEQ ID No. 9.

15. A mutant deregulated 3-phosphoglycerate-dehydrogenase, which in comparison to a wild type 3-phosphoglycerate dehydrogenase has reduced feedback inhibition by L-serine according to claim 11 with an amino acid sequence consisting of SEQ ID No. 10.

16. A mutant deregulated 3-phosphoglycerate-dehydrogenase according to claim 11, consisting of SEQ ID NO: 11 where said mutant deregulated 3-phosphoglycerate-dehydrogenase has a reduced feedback inhibition by L-serine compared to the wild type 3-phosphoglycerate dehydrogenase.

17. A polypeptide according to claim 11 derived from coryneform bacteria.

18. A polypeptide according to claim 11 derived from *Corynebacterium* or *Brevibacterium*.

19. A polypeptide according to claim 11 derived from *Corynebacterium glutamicum* or *Brevibacterium flavum*.

20. A microorganism containing a nucleic acid according to claim 1, claim 2, claim 3, claim 4 or claim 5 in replicable form and which by comparison with the wild type microorganism is expressed in an amplified manner and/or has its copy number increased.

21. A microorganism according to claim 20 further comprising regulatory sequences operatively linked thereto and additional nucleotide sequences for selection, replication, in a host cell or for integration in the host cell genome.

22. A microorganism according to claim 20 expressing at least one amino acid sequence consisting of SEQ ID NO. 7, SEQ ID NO. 8, SEQ ID NO. 9, SEQ ID NO. 10 or SEQ ID NO. 11 which, by comparison to the corresponding wild type microorganism shows an active deregulated 3-phosphoglycerate-dehydrogenase with reduced feedback inhibition.

23. The microorganism according to claim 20 that is a Coryneform bacterium.

24. The microorganism according to claim 20 that belongs to the familia *Corynebacterium* or *Brevibacterium*.

25. The microorganism according to claim 24 that belongs to *Corynebacterium glutamicum* or *Brevibacterium flavum*.

26. A probe for identifying and/or isolating genes which encode a deregulated 3-phosphoglycerate dehydrogenase participating in the biosynthesis of L-serine, said probe consisting of SEQ ID NO. 13, SEQ ID NO. 14, SEQ ID NO. 15, SEQ ID NO. 16, SEQ ID NO. 17, SEQ ID NO. 18, or SEQ ID NO.19 and containing a marker suitable for detection.

27. A method for microbially producing L-serine from a carbohydrate, fat or oil, fatty acid, alcohol or organic acid, in a culture medium, containing nitrogen sources and phosphorous sources, which comprises the steps of:
a) providing at least one nucleic acid encoding a deregulated 3-phosphoglycerate dehydrogenase, selected from the group consisting of SEQ ID NO. 1, SEQ ID NO. 2, SEQ ID NO. 3, SEQ ID NO. 4 and SEQ ID NO. 5, isolated from a Coryneform bacterium, and transformed into a Coryneform bacterium, and then expressed to form the deregulated 3-phosphoglycerate dehydrogenase, whereby the gene expression and/or the activity of the corresponding encoded deregulated 3-phosphoglycerate dehydrogenase is increased with respect to the corresponding microorganism which has not been genetically altered;
b) microbially producing L-serine by expressing the at least one nucleic acid which encodes a deregulated 3-phosphoglycerate dehydrogenase in said genetically modified microorganism from step a) to microbially convert said carbohydrate, fat or oil, fatty acid, alcohol or organic acid in said culture medium to L-serine; and
c) isolating the correspondingly formed L-serine from the culture medium.

28. The method for microbially producing L-serine from a carbohydrate, fat or oil, fatty acid, alcohol or organic acid, in a culture medium, defined in claim 27 wherein the nucleic acid which encodes a deregulated 3-phosphoglycerate dehydrogenase is SEQ ID NO.1.

* * * * *